(12) United States Patent
Rickus et al.

(10) Patent No.: US 8,183,043 B2
(45) Date of Patent: May 22, 2012

(54) SOL-GEL MATERIALS FOR CELLULAR MODULATION

(75) Inventors: Jenna Leigh Rickus, West Lafayette, IN (US); Sabrina S. Jedlicka, Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 368 days.

(21) Appl. No.: 12/445,015

(22) PCT Filed: Oct. 11, 2007

(86) PCT No.: PCT/US2007/081122
§ 371 (c)(1),
(2), (4) Date: Apr. 9, 2009

(87) PCT Pub. No.: WO2008/057709
PCT Pub. Date: May 15, 2008

(65) Prior Publication Data
US 2010/0221836 A1 Sep. 2, 2010

Related U.S. Application Data

(60) Provisional application No. 60/850,893, filed on Oct. 11, 2006.

(51) Int. Cl.
*C12N 5/00* (2006.01)
*C12N 5/02* (2006.01)
*A61K 38/10* (2006.01)
*A61K 38/08* (2006.01)

(52) U.S. Cl. ..... 435/404; 514/21.5; 514/21.6; 514/21.7; 514/21.8

(58) Field of Classification Search .................. None
See application file for complete search history.

(56) References Cited

U.S. PATENT DOCUMENTS

| | | | |
|---|---|---|---|
| 6,022,748 A * | 2/2000 | Charych et al. | ............... 436/527 |
| 2004/0023391 A1 | 2/2004 | Fang et al. | |
| 2004/0202637 A1 | 10/2004 | Yoshioka et al. | |
| 2006/0149036 A1 | 7/2006 | Stupp et al. | |

FOREIGN PATENT DOCUMENTS

WO WO 03/068806 * 8/2003

OTHER PUBLICATIONS

Gill. Bio-doped Nanocomposite Polymers: Sol-Gel Bioencapsulates. Chem. Matter. 2001, vol. 13, p. 3404-3421.*
Coradin et al. Interactions of Amino-Containing Peptides with Sodium Silicate and Colloidal Silica: A Biomimetic Approach of Silicification. Langmuir 2002, vol. 18, pp. 2331-2336.*
Schubert et al. Hybrid Inorganic-Organic Materials by Sol-Gel Processing of Organofunctional Metal Alkoxides. Reviews, Chem Mater, 1995, vol. 7, pp. 2010-2027.*
Jones et al. Bioactive glass scaffolds for bone regeneration and their hierarchichal characterisation. Proc I Mech E. Part H: J Engineering in Medicine, 2010. vol. 224, pp. 1373-1387.*
Jedlicka et al. Controllable Surface Expression of Bioactive Peptides Incorporated into a Silica Thin Film Matrix. J Phys Chem. C. 2010, vol. 114, pp. 342-344.*
Sepulveda et al. Bioacitve sol-gel foams for tissue repair. J Biomed Mat Res. 2001.vol. 59, Issue 2, pp. 340-348.*
Betancor, Lorena, et al., Different Mechanisms of Protein Immobilization on Glutaraldehyde Activated Supports: Effect of Support Activation and Immobilization Conditions, 2006, *Enzyme and Microbial Technology*, No. 39, pp. 877-882.
Briones, C., et al., "Ordered Self-Assembled Monolayers of Peptide Nucleic Acids with DNA Regognition Capability", Nov. 12, 2004, *Physical Review Letter*, vol. No. 93, No. 20, pp. 28103-1/28103-4.
Faucheux, N., et al., "Self-Assembled Monolayers with different Terminating groups as Model Substrates for Cell Adhesion Studies", 2004, *Biomaterials*, No. 25, pp. 2721-2730.
Fields, C. G., et al., "HBTU Activation for Automated Fmoc Solid-Phase Peptide Synthesis", 1991, *Peptide Research*, vol. 4, No. 2, pp. 95-101.
Jedlicka, Sabrina S., et al, "Sol-Gel Derived Materials as Substrates for Neuronal Differentiation: Effects of Surface Features and Protein Conformation", 2006, *Journal of Materials Chemistry*, No. 16, pp. 3221-3230.
Kim, Taek Gyoung, et al., "Surface Punctionalized Electrospun Biodegradable Nanofibers for Immobilization of Bioactive Molecles", 2006, *Biotechnology Progress*, No. 22, pp. 1108-1113.
McBurney, Michael W., et al., "Isolation of Male Embryonal Carcinoma Cells and Their Chromosome Replication Patterns", 1982, *Developmental Biology*, vol. 89, pp. 503-508.
McBumey, Michael W., "P19 Embryonal Carcinoma Cells", 1993, *International Journal of Developmental Biology*, vol. 37, pp. 135-140.

* cited by examiner

*Primary Examiner* — Marcela M Cordero Garcia
(74) *Attorney, Agent, or Firm* — Barnes & Thornburg LLP

(57) ABSTRACT

A modified sol-gel material and method of making the same is provided herein. More particularly, sol-gels disclosed herein have been modified to have one or more bioactive peptides covalently bound to the surface of the sol-gel. In one embodiment the peptide presenting sol-gels are prepared as thin film coatings and in a further embodiment the sol-gels are combined with living cells. The present disclosure is also directed to a novel one vessel reaction process for preparing the sol-gel-based peptide material.

23 Claims, 8 Drawing Sheets

SOL-GEL MATERIALS FOR CELLULAR MODULATION

CROSS REFERENCE TO RELATED APPLICATIONS

This application is a U.S. national application under 35 U.S.C. & 371(b) of International Application Serial No. PCT/US2007/081122 filed Oct. 11, 2007, which claims priority to U.S. Provisional Patent Application Ser. No. 60/850,893 filed on Oct. 11, 2006, the entire disclosure of which is hereby incorporated by reference.

GOVERNMENT RIGHTS

This invention was made with government support under grant number NA/IND010674 awarded by the USDA/NIFA. The U.S. Government has certain rights in the invention.

BACKGROUND OF THE INVENTION

The integration of cells into engineered devices has considerable potential in implantable biomedical therapeutics, stem cell environments and cell-based biosensors. These applications require that cells survive on or in inorganic or hybrid materials and carry out normal metabolism, proliferation and differentiation. The microenvironment immediately surrounding the cells substantially impacts cellular processes and ultimately the final fate of the cell. The presentation and characterization of bioactive molecules at the surface of inorganic and hybrid materials, therefore, is an important factor in a material's capability.

Sol-gel derived materials produced under biologically benign conditions have demonstrated an ability to serve as substrates or supports for numerous cell types including mammalian cells, bacteria, and yeast. The sol-gel method of producing amorphous inorganic or organically modified porous solids from liquid precursors is a functionally diverse technique that allows for simple manipulation of both chemical features as well as nanoscale morphology through processing procedures. Metal alkoxides, such as tetramethoxysilane, are common liquid precursors. Organically modified silica (ormosil) can be created by modifying the functional groups on the silane precursors (see Briones, et al., *Physical Review Letters* 2004, 93, (20)), resulting in a material that is decorated with the chemical functionality of choice.

As disclosed herein a novel sol-gel method is provided for producing biologically active peptide-modified porous silica matrices from peptide-silane precursors. A variety of materials have been prepared that have taken advantage of known cell binding peptide sequences from proteins, such as extracellular matrix proteins and cell-cell adhesion proteins, at the biointerface to enhance cell adhesion. Peptides such as the RGD group from fibronectin type III repeats, and the YIGSR peptide from laminin, enhance cell adhesion of various cell types to two dimensional materials. Previous work has generally presented such bioactive peptides as a self-assembled monolayer immobilized using various chemistries, including thiol attachment (Faucheux, et al., Biomat. 2004, 25, 2721), covalent assembly using amine linkers (Kim, T. G.; Park, T. G. Biotechnology Progress 2006, 22, 1108), or physioadsorption onto the surface of interest (Betancor, et al., Enzyme and Microbial Technology 2006, 39, 877). Controlling the percentage of the peptides at the surface is difficult to achieve, as multilayer organization and environmental factors all play a role in the efficiency of the coupling chemistry, leading to a lack of consistency from surface to surface.

Accordingly, there is a need for a sol-gel chemistry that allows for a simple single reaction vessel synthesis while allowing for precise concentration manipulation of added peptides. The present invention provides such a process, producing a sol-gel wherein one or more peptides of choice are covalently linked to the resulting film such that the peptides do not leach out of the material matrix.

SUMMARY OF THE INVENTION

A modified sol-gel material and method of making the same is provided herein. More particularly, the sol-gels disclosed herein have been modified to have one or more bioactive peptides covalently bound to the sol-gel matrix. The method allows for the control and calibration of peptide density on the surface of the material. In one embodiment the peptide presenting sol-gels are prepared as thin film coatings. In one embodiment the coatings are applied to biological implants prior to their implantation. In one embodiment the sol-gels are combined with living cells.

In accordance with one embodiment the sol-gel-based hybrid material comprises at least one peptide-silane complex bound within a silica thin film, wherein the peptide silane complex is functional in modulating cell adhesion, signaling or differentiation. In one embodiment the peptide-silane complex may comprise any of the peptides shown in Table 1 below, or any combination thereof. However, the present disclosure is intended to encompass any peptide-silane that can be synthesized using standard techniques known to those skilled in the art.

TABLE 1

Examples of peptides suitable for use in peptide-silane complexes

| Peptide | Origin |
|---|---|
| SIDRVEPYSSTAQG (SEQ ID NO: 18) | NCAM |
| CSVTCGG (SEQ ID NO: 19) | Thrombospondin |
| CYFQRYLI (SEQ ID NO: 6) | Laminin α |
| RDIAEIIKDIG (SEQ ID NO: 12) | Laminin γ1 |
| YAVTGRGDSPAS (SEQ ID NO: 11) | Fibronectin Type III repeat |
| DPGYIGSRGA (SEQ ID NO: 13) | Laminin |
| VSWFSRHRYSPFAVS (SEQ ID NO: 20) | Laminin, α6β1 Integrin |
| AASIKVAVSADRG (SEQ ID NO: 21) | Laminin α1 |
| NDNIDPNAVA (SEQ ID NO: 14) | Tenascin, Laminin |
| SLVRNRRVITIQG (SEQ ID NO: 22) | Laminin α1 |

The present disclosure is also directed to a novel one vessel reaction process for preparing the sol-gel-based hybrid material. The method comprises providing a peptide-silane composition, and combining the peptide-silane composition with a second composition comprising silicates to form a mixture.

The mixture is then coated onto a surface of a support and the mixture is gelled to form a porous silica network presenting covalently bound peptides. The peptide-silica hybrid can be designed to fit any geometry or presentation, such as bulk monoliths, powders, coatings, aerogels, or nanoparticles.

Additional features of the present disclosure will become apparent to those skilled in the art upon consideration of the following detailed description of embodiments exemplifying the best mode of carrying out the subject matter of the disclosure as presently perceived.

DETAILED DESCRIPTION

Definitions

Figure 1A:
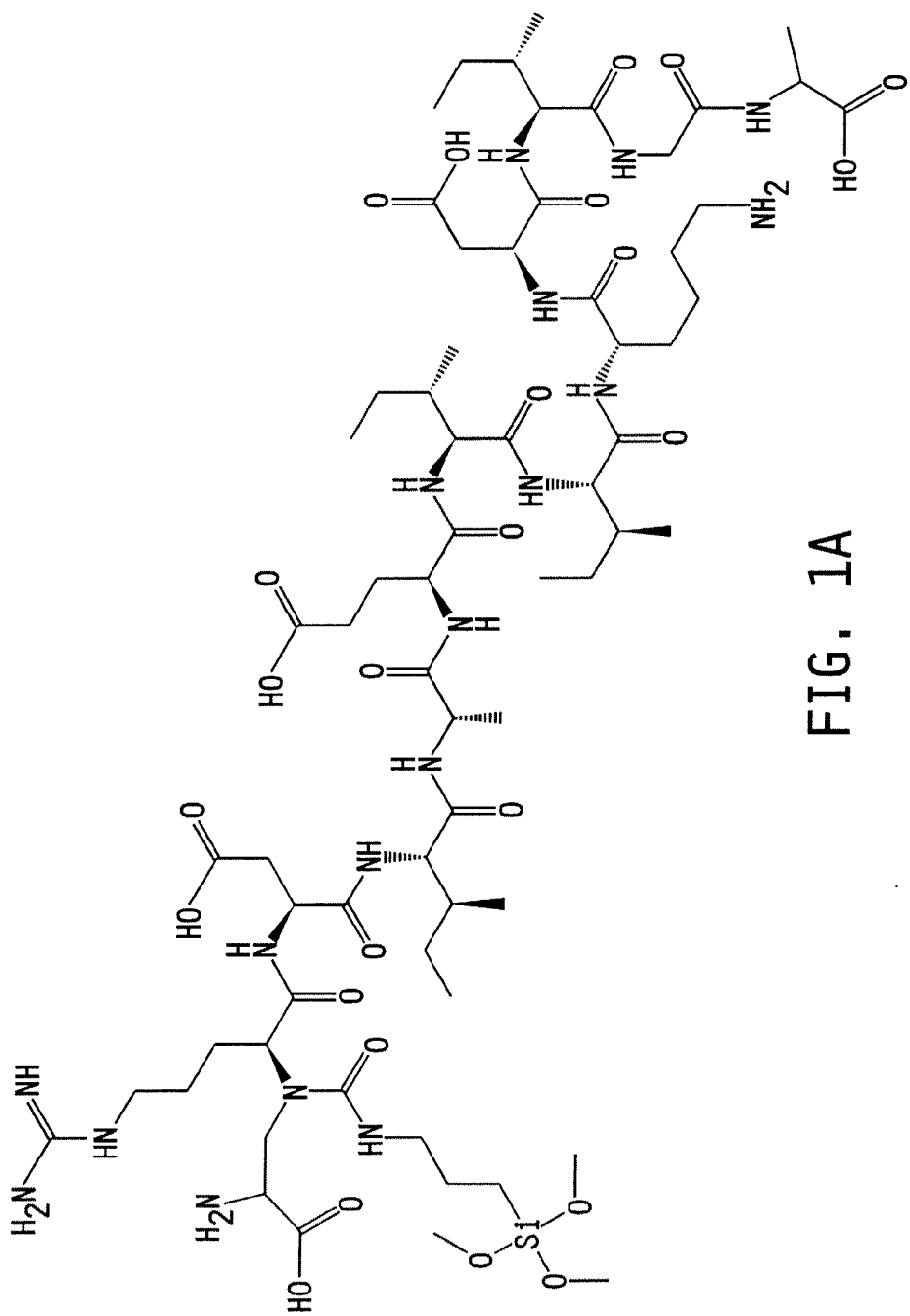
FIGS. 1A-1D represents the structures of four specific peptide-silane precursors: NID Silane, RGD Silane, KDI Silane and YIG Silane, respectively.
Figure 1B:
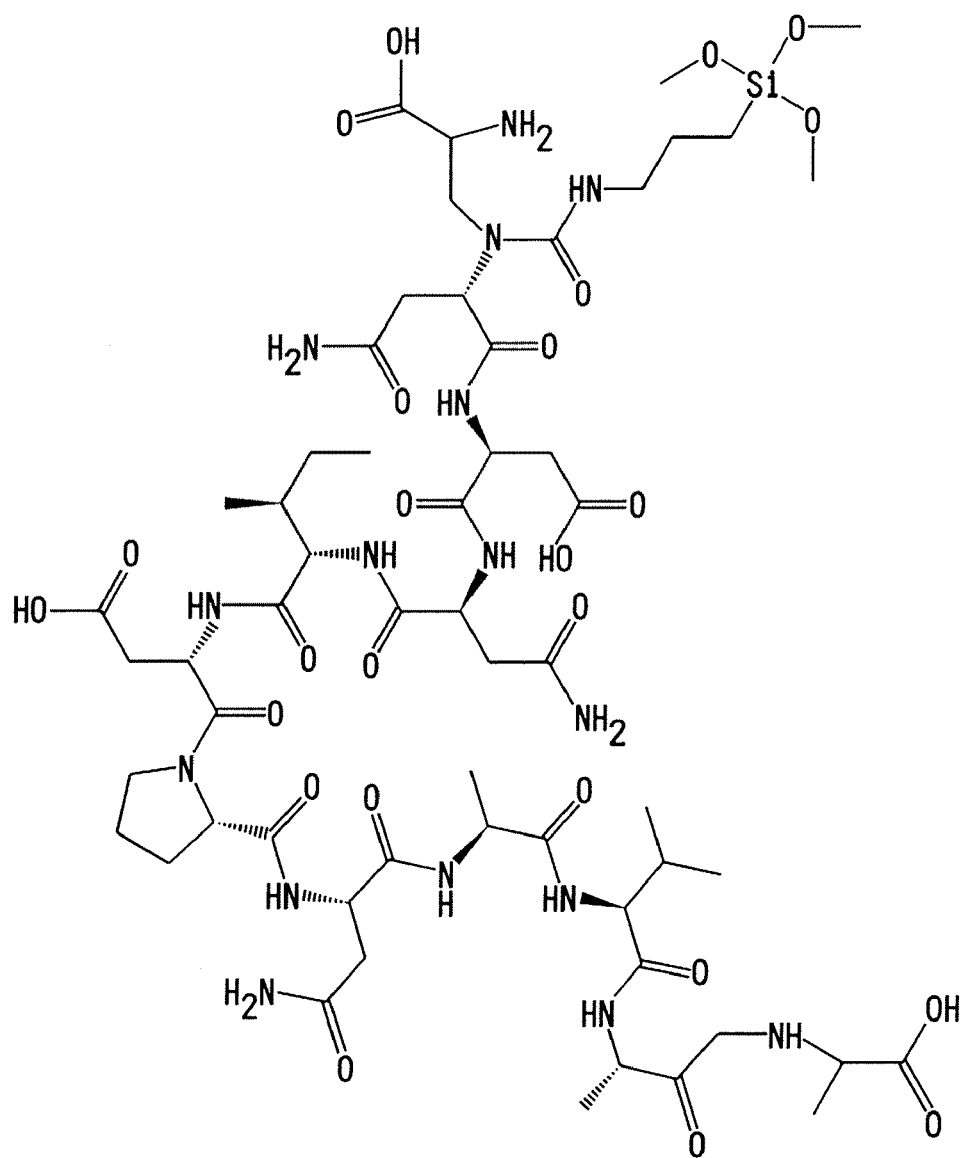
Figure 1C:
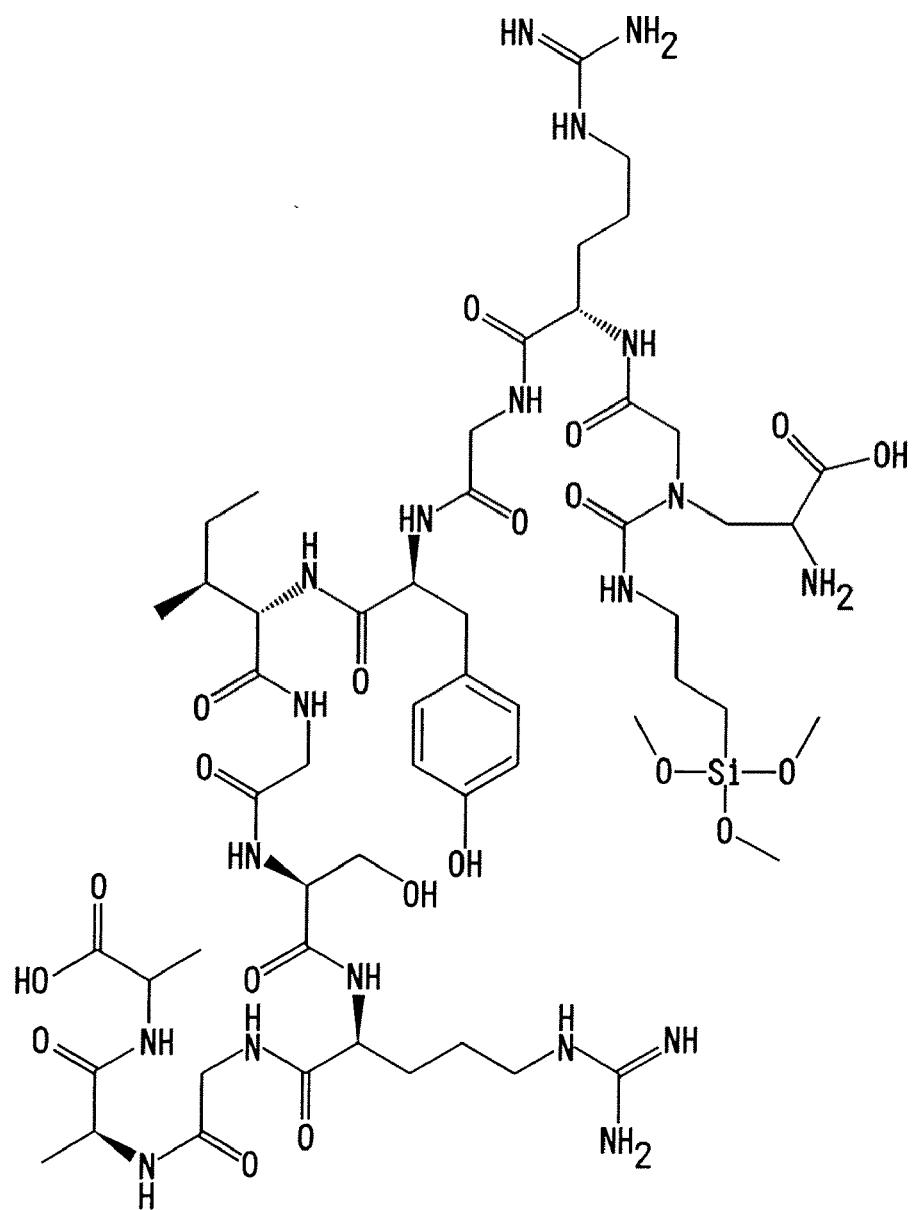
Figure 1D:
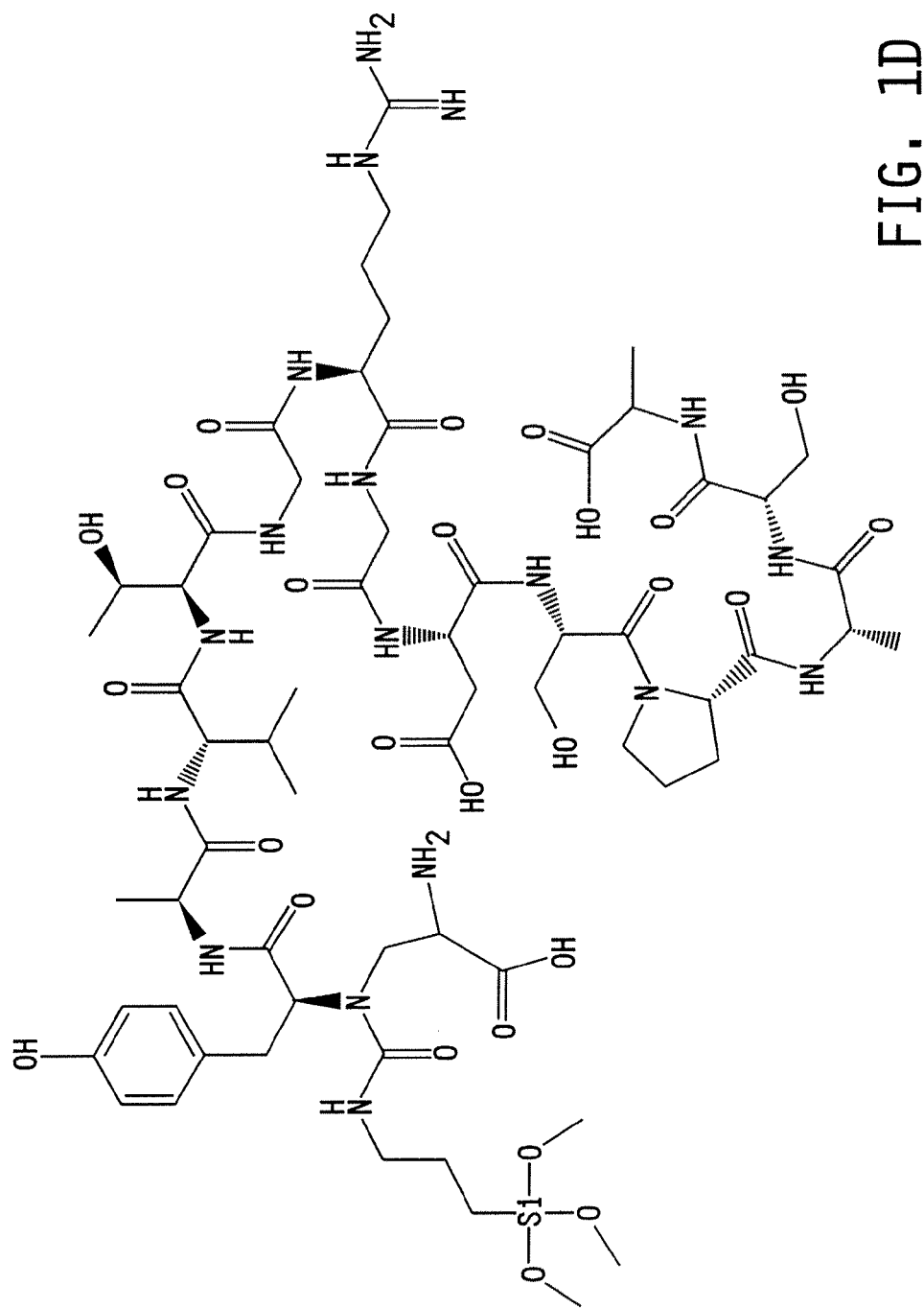

In describing and claiming the invention, the following terminology will be used in accordance with the definitions set forth below. Abbreviated peptide codes are used throughout as a description, and include the following (RGD, IKV, YIG, KDI, CYF, SLVR, VSW, SIDR); which may or may not correspond directly to the biologically functional region of the full length peptide-silane of interest.

As used herein the term NID peptide or NID Silane refers to a compound that comprises an amino acid sequence that contains the contiguous amino acids NID and may include additional amino acids in addition to those three amino acids.

As used herein the term RGD peptide or RGD Silane refers to a compound that comprises an amino acid sequence that contains the contiguous amino acids RGD and may include additional amino acids in addition to those three amino acids.

As used herein the term KDI peptide or KDI Silane refers to a compound that comprises an amino acid sequence that contains the contiguous amino acids KDI and may include additional amino acids in addition to those three amino acids.

As used herein the term YIG peptide or YIG Silane refers to a compound that comprises an amino acid sequence that contains the contiguous amino acids YIG and may include additional amino acids in addition to those three amino acids.

As used herein the term sol-gel refers a composition formed from a solution containing metal alkoxide or metal chloride colloidal precursors (a sol), which undergo hydrolysis and polycondensation reactions to form an inorganic network containing a liquid phase (gel). The formed matrix can be subjected to a drying process to remove the liquid phase from the gel thus forming a porous material. For example, in one embodiment a sol-gel is formed from orthosilicates, including for example, tetramethylorthosilicate and tetraethylorthosilicate.

A "bioactive peptide" relates to peptides, which are capable of exerting a biological effect on cells grown in vitro and/or in vivo. The biological effect may be either a qualitative or quantitative change in the cell's physiology.

As used herein the term "peptide-silane" is intended to encompass a compound comprising a peptide covalently bound to a silica bearing moiety, including for example silicates.

The term "$C_1$-$C_n$ alkyl" wherein n is an integer greater than or equal to 2, as used herein, represents a branched or linear alkyl group having from one to the specified number of carbon atoms. For example, $C_1$-$C_4$ alkyl groups include, but are not limited to, methyl, ethyl, n-propyl, iso-propyl, butyl, iso-butyl, sec-butyl, tert-butyl and the like.

EMBODIMENTS

As described herein chemically modified hybrid sol-gel materials are provided, as well as a novel method for making the same. In one embodiment the sol-gel materials are modified to have bioactive peptides covalently bound to the sol-gel matrix, wherein the peptides mimic the natural biological signals. Such materials increase the potential for the creation of novel hybrid cell-silicon devices and may be useful engineering tools for pre-surgical priming and manipulation of cells.

In accordance with one embodiment a simple one reaction vessel methodology is provided for preparing sol-gel cell substrates that have been modified to present bioactive peptides. In one embodiment the bioactive peptides present native cellular signals. More particularly, the method advantageously allows for the covalent binding of one or more peptides to the surface of a porous sol-gel in a controlled manner, allowing for the presentation of specific ratios of the individual bioactive peptides. Advantageously, as described in detail in Examples 2 and 3 of the present disclosure the peptide-silane compounds are incorporated into a sol-gel at near 100% efficiencies. Accordingly, the concentration of the covalently bound peptides in the final sol-gel product is directly linear with respect to the concentration of the peptide-silane present in the precursor liquid peptide-silane composition. Therefore, using the methods described herein, the peptide concentration of one or more covalently bound peptides in the formed sol-gel can be predetermined based on the concentration of the peptide silane(s) in the precursor liquid peptide-silane composition.

In one embodiment a method for preparing a peptide presenting sol-gel is provided wherein one or more peptides are covalently bound to the surface of the sole-gel matrix. The method comprises combining a first peptide-silane composition with a hydrolyzed silicate composition to form a mixture. The mixture is then gelled, wherein the peptide-silane compounds are dispersed within the formed sol-gel, thus forming a silica matrix comprising peptides covalently bound to the matrix surface in a predetermined concentration. Advantageously, sol-gels can also be prepared wherein the sol-gel presents multiple distinct peptides covalently bond to the sol-gel matrix and wherein the relative concentration of each distinct peptide to one another is predetermined.

The peptide-silanes themselves can be formed using standard techniques to covalently bind a peptide to a silicon bearing compound. In accordance with one embodiment a peptide-silane is formed using carbonyldiimidazole (CDI) as a linking molecule. However other linking agents known to those skilled in the art can also are used. In one embodiment the peptide is covalently bound to a silicate having the general formula (N-amino($C_1$-$C_4$)tri($C_1$-$C_4$)oxysilane, and more particularly the silicate is selected form the group consisting of (3-aminopropyl)trimethoxysilane, (3-aminopropyl)triethoxysilane, and (3-aminopropyl)trimethoxysilane. In accordance with one embodiment, the peptide moiety of the peptide-silane complex is synthesized using standard solid state techniques and the linkage of the silicon moiety at the N-terminal end of the growing peptide is the last step of the synthesis.

Advantageously, applicants disclosed methodology allows for greater ease of synthesis while allowing for tight control of the compositions of the final product. In accordance with one embodiment the method comprises the preparation of a first composition comprising the peptide-silane (at a predetermined concentration) which is then mixed with a standard second composition comprising an orthosilicate. In one embodiment the mole ratio of total peptide-silane to silicon dioxide in the first composition is selected from a range of about 0.001 to about 0.5 and more typically the mole ratio of total peptide-silane to silicon dioxide is about 0.0025 to about 0.2. In one embodiment the mole ratio of total peptide-silane to silicon dioxide in the first composition is selected from a range of about 0.025 to about 0.1. The orthosilicate of the second composition is hydrolyzed under acid conditions to produce a silica sol prior to combining the first and second compositions. The ratio (v/v) of the peptide-silane composition to the orthosilicate composition in the resultant mixture can be varied depending on the application, but can be selected from volume to volume ratios of 9:1, 8:2, 7:3, 6:4 or 1:1. In one embodiment the volume to volume ratio of the peptide-silane composition to the orthosilicate composition is 7:3. In addition to the silica compositions, a low molecular weight alcohol such as methanol can be added to the mixture to slow the condensation of the gel.

In accordance with one embodiment the precursor sol mixture is deposited on a substrate to form a film using standard techniques, including by dip-coating or spin-coating. In accordance with one embodiment a thin film is formed on a substrate by dipping the substrate into the precursor sol mixture at a rate no faster than 35 mm/second. In one embodiment the substrate is immersed in the precursor sol mixture and removed at a rate of about 40, 30, 20, or 10 mm/second. In another embodiment the substrate is dipped multiple times into one, or more, precursor sol mixtures (either the same or differing from each other) to create multiple layers on a particular substrate. The resulting layers may differ from one another based on the pore size of the sol-gel (i.e., fiber density) or by the peptides that are presented by each layer (either in terms of types of peptides presented or the relative quantity of one or more of the peptides). In an alternative embodiment the precursor sol mixture can be cast into a suitable container with the desired shape (e.g. to obtain a monolithic ceramics, glasses, fibers, membranes, aerogels), or used to synthesize powders (e.g. microspheres, nanospheres).

The peptide component of the peptide-silanes may comprise naturally occurring amino acids or synthetic (non-naturally occurring) amino acids or a mixture of naturally occurring and synthetic amino acids. Synthetic or non-naturally occurring amino acids refer to amino acids that do not naturally occur in vivo but which, nevertheless, can be incorporated into the peptide structures described herein. A general reference to a "peptide" or "amino acid" is intended to encompass the possible inclusion of synthetic or non-naturally occurring amino acids. In addition, the present disclosure also encompasses the possible further modification of the covalently bound peptides to include additional biochemical functional groups such as acetate, phosphate, lipid and carbohydrate moieties. The covalently bound peptides can be of any length, however, typically they are less than 100 amino acids in length and more typically less than 50 amino acids in length, and in one embodiment the peptides are 30 amino acids or less in length. In one embodiment the peptides are selected to be approximately 3-30 amino acids in length, and more particularly about 6 to 30 amino acids, and in one embodiment about 6 to 14 amino acids in length to limit secondary structure formation on the resin.

The nanotexture of the modified sol-gel films formed in accordance with the present disclosure is impacted by the selection of the peptide and the concentration of the formed peptide-silane in the sol-gel. Surface features of a cell substrate are known to be important to cellular processes. For example, bulk silica monoliths, with features ranging from 100-250 nm, are non-permissive to PC12 neuron adhesion, whereas, thin-film sol-gel morphology, with height features ranging between 25-100 nm, supports PC12 neuronal adhesion. Accordingly, in one embodiment a modified sol-gel film is provided wherein the surface features are less than 100 nm.

The nanotexture of the silica modified films does not vary dramatically from the native silica films prepared in the standard way.

In accordance with one embodiment a modified sol-gel is provided wherein the sol-gel comprises two or more peptides covalently bound to the sol-gel matrix wherein the peptides differ from one another by their amino acid sequence or by the presence of a biochemical functional group. In one embodiment the peptide is a bioactive peptide. In one embodiment the peptide is 3-30 amino acids in length and comprises an amino acid sequence selected from the group consisting of RGD (SEQ ID NO:1), KDI (SEQ ID NO:2), YIG (SEQ ID NO:3), NID (SEQ ID NO:4), RNNR (SEQ ID NO:5), SNNR (SEQ ID NO: 24) and CYFQRYLI (SEQ ID NO:6). In one embodiment the peptide moiety of the peptide-silane component comprises an amino acid sequence selected from the group consisting of YIGSR (SEQ ID NO:7), GRGDNP (SEQ ID NO:8), RDIAEIIKDISLVRNRR (SEQ ID NO: 25), CYFQRYLI (SEQ ID NO:6), NDNIDPNAVA (SEQ ID NO:10), YAVTGRGDSPAS (SEQ ID NO:11), RDIAEIIK-DIG (SEQ ID NO:12), DPGYIGSRGA (SEQ ID NO:13), ANDNIDPNAVAA (SEQ ID NO:14), AYAVTGRGDSPASA (SEQ ID NO:15), ARDIAEIIKDIGA (SEQ ID NO:16) ADPGYIGSRGAA (SEQ ID NO:17), SIDRVEPYSSTAQG (SEQ ID NO: 18), CSVTCGG (SEQ ID NO: 19), VSWFS-RHRYSPFAVS (SEQ ID NO: 20), AASIKVAVSADRG (SEQ ID NO: 21) and SLVRNRRVITIQG (SEQ ID NO: 22). In one embodiment the peptide moiety of the peptide-silane component comprises an amino acid sequence selected from the group consisting of NDNIDPNAVA (SEQ ID NO:10), YAVTGRGDSPAS (SEQ ID NO:11), RDIAEIIKDIG (SEQ ID NO:12) and DPGYIGSRGA (SEQ ID NO:13). In one embodiment the peptide moiety of the peptide-silane component comprises DPGYIGSRGA (SEQ ID NO:13) and/or YAVTGRGDSPAS (SEQ ID NO:11).

In accordance with one embodiment a nano-textured sol-gel-based hybrid material for cellular modulation is prepared. In one embodiment the sol-gel based hybrid material comprises a film that has been coated onto a biological implant prior to implantation. Alternatively, the sol-gel based hybrid material may be used to supplement in vitro culturing of cells either as an additive to media or as a film for coating labware, including cell culture substrates.

In accordance with one embodiment a method is provided for differentiating totipotent or pluripotent cells along a defined pathway, or to change the end cell phenotype of a homogeneous cell population. The method comprises contacting the cells (either in vitro or in vivo) with a sol-gel composition disclosed herein and culturing the cells using standard culture techniques, wherein the peptides displayed by the sol-gel have been selected based on their known bioactivities to direct cell differentiation. Similarly, a method of altering, or inducing the formation of, the relative ratios of the cell phenotypes in a heterogeneous cell population is provided wherein the heterogeneous cell population (or an initially homogenous cell population) is contacted (either in vitro or in vivo) with the sol-gel compositions disclosed herein.

In accordance with one embodiment a method is provided for enhancing the ability of cells to adhere and survive on an inorganic surface. The method comprises the steps of contacting the cells (either in vitro or in vivo) with the sol-gel composition of the present invention. In accordance with one embodiment the cells are contacted with a sol-gel composition comprising a covalently bound peptide comprising an amino acid sequence selected from the group consisting of RGD (SEQ ID NO:1), KDI (SEQ ID NO:2), YIG (SEQ ID NO:3), NID (SEQ ID NO:4). In one embodiment the sol-gel comprises two different, covalently bound peptides, wherein the different peptides comprise an amino acid sequence selected from the group consisting of RGD (SEQ ID NO:1), KDI (SEQ ID NO:2), YIG (SEQ ID NO:3), NID (SEQ ID NO:4). In one embodiment the sol-gel comprises three different, covalently bound peptides, wherein the different peptides comprise an amino acid sequence selected from the group consisting of RGD (SEQ ID NO:1), KDI (SEQ ID NO:2), YIG (SEQ ID NO:3), NID (SEQ ID NO:4). In one embodiment the sol-gel comprises four different, covalently bound peptides, wherein the different peptides comprise an amino acid sequence of RGD (SEQ ID NO:1), KDI (SEQ ID NO:2), YIG (SEQ ID NO:3), NID (SEQ ID NO:4), respectively.

In one embodiment the sol-gel comprises two different, covalently bound peptides, wherein the different peptides comprise an amino acid sequence selected from the group consisting of RNNR (SEQ ID NO:5), CYFQRYLI (SEQ ID NO:6), YIGSR (SEQ ID NO:7), GRGDNP (SEQ ID NO:8), RDIAEIIKDISLVRNRR (SEQ ID NO: 25), NDNIDPNAVA (SEQ ID NO:10), YAVTGRGDSPAS (SEQ ID NO:11), RDI-AEIIKDIG (SEQ ID NO:12), DPGYIGSRGA (SEQ ID NO:13), ANDNIDPNAVAA (SEQ ID NO:14), AYAVT-GRGDSPASA (SEQ ID NO:15), ARDIAEIIKDIGA (SEQ ID NO:16) ADPGYIGSRGAA (SEQ ID NO:17), SIDRVE-PYSSTAQG (SEQ ID NO: 18), CSVTCGG (SEQ ID NO: 19), VSWFSRHRYSPFAVS (SEQ ID NO: 20), AASIKVAVSADRG (SEQ ID NO: 21) and SLVRNRRVI-TIQG (SEQ ID NO: 22). In one embodiment the sol-gel comprises three different, covalently bound peptides, wherein the different peptides comprise an amino acid sequence selected from the group consisting of RNNR (SEQ ID NO:5), CYFQRYLI (SEQ ID NO:6), YIGSR (SEQ ID NO:7), GRGDNP (SEQ ID NO:8), RDIAEIIKDISLVRNRR (SEQ ID NO: 25), NDNIDPNAVA (SEQ ID NO:10), YAVT-GRGDSPAS (SEQ ID NO:11), RDIAEIIKDIG (SEQ ID NO:12), DPGYIGSRGA (SEQ ID NO:13), ANDNIDP-NAVAA (SEQ ID NO:14), AYAVTGRGDSPASA (SEQ ID NO:15), ARDIAEIIKDIGA (SEQ ID NO:16) ADPGYIGSR-GAA (SEQ ID NO:17), SIDRVEPYSSTAQG (SEQ ID NO: 18), CSVTCGG (SEQ ID NO: 19), VSWFSRHRYSPFAVS (SEQ ID NO: 20), AASIKVAVSADRG (SEQ ID NO: 21) and SLVRNRRVITIQG (SEQ ID NO: 22).

In accordance with one embodiment a kit for preparing a sol-gel having a defined concentration of peptides covalently bound to the sol-gel is provided. The kit comprises the necessary reagents for preparing a sol-gel in accordance with the methods disclosed herein. In one embodiment the kit comprises a plurality of first containers, wherein each of the first containers contains one peptide-silane compound suitable for forming a sol-gel. A second container of the kit comprises a silicate, and more particularly in one embodiment, an orthosilicate, including for example, tetramethylorthosilicate or tetraethylorthosilicate. Accordingly, the kit allows one to prepare a sol-gel having a predetermined concentration of one or more peptides covalently bound to the formed sol-gel, as well as determine which of the plurality of peptides provided with the kit to include in the formed sol-gel. In one embodiment the second container of the kit comprises a silicate selected from the group consisting of tetraethylorthosilicate, tetramethylorthosilicate and tetrapropylorthosilicate. In a further embodiment the kit comprises peptide-silane species wherein the peptide moiety of the peptide-silane comprises an amino acid sequence selected from the group consisting of RGD (SEQ ID NO:1), KDI (SEQ ID NO:2), YIG (SEQ ID NO:3), NID (SEQ ID NO:4), RNNR (SEQ ID NO:5), CYFQRYLI (SEQ ID NO:6), YIGSR (SEQ ID NO:7), GRGDNP (SEQ ID NO:8), RDIAEIIKDISLVRNRR (SEQ ID NO: 25), NDNID-PNAVA (SEQ ID NO:10), YAVTGRGDSPAS (SEQ ID NO:11), RDIAEIIKDIG (SEQ ID NO:12), DPGYIGSRGA (SEQ ID NO:13), ANDNIDPNAVAA (SEQ ID NO:14), AYAVTGRGDSPASA (SEQ ID NO:15), ARDIAEIIKDIGA (SEQ ID NO:16) ADPGYIGSRGAA (SEQ ID NO:17), SIDRVEPYSSTAQG (SEQ ID NO: 18), CSVTCGG (SEQ ID NO: 19), VSWFSRHRYSPFAVS (SEQ ID NO: 20), AASIKVAVSADRG (SEQ ID NO: 21) and SLVRNRRVITIQG (SEQ ID NO: 22). The kit may further include additional buffers and a variety of containers, e.g., vials, tubes, bottles, and the like for preparing sol-gel compositions. Preferably, the kits will also include instructions for use.

The present disclosure also encompasses the nano-textured sol-gel materials formed using the methods of the present disclosure. In accordance with one embodiment the nano-textured sol-gel-based hybrid material comprises at least one peptide-silane complex bound to a silica thin film, wherein the peptide silane complex functions in modulating neuronal signaling or differentiation. In one embodiment the modified sol-gel comprises two or more peptides covalently bound to the sol-gel matrix, wherein the two or more peptides comprise an amino acid sequence independently selected from the group consisting of RGD (SEQ ID NO:1), KDI (SEQ ID NO:2), YIG (SEQ ID NO:3) and NID (SEQ ID NO:4). In one embodiment the two or more peptides comprise an amino acid sequence independently selected from the group consisting of RGD (SEQ ID NO:1), KDI (SEQ ID NO:2), YIG (SEQ ID NO:3), NIDSLVRNRR (SEQ ID NO:4), RNNR (SEQ ID NO:5), and CYFQRYLI (SEQ ID NO:6), YIGSR (SEQ ID NO:7), GRGDNP (SEQ ID NO:8), RDIAEIIKDI (SEQ ID NO:9), NDNIDPNAVA (SEQ ID NO:10), YAVTGRGDSPAS (SEQ ID NO:11), RDIAEIIKDIG (SEQ ID NO:12), DPGYIGSRGA (SEQ ID NO:13), ANDNIDPNAVAA (SEQ ID NO:14), AYAVTGRGDSPASA (SEQ ID NO:15), ARDIAEIIKDIGA (SEQ ID NO:16), ADPGYIGSRGAA (SEQ ID NO:17), SIDRVEPYSSTAQG (SEQ ID NO: 18), CSVTCGG (SEQ ID NO: 19), VSWFSRHRYSPFAVS (SEQ ID NO: 20), AASIKVAVSADRG (SEQ ID NO: 21) and SLVRNRRVITIQG (SEQ ID NO: 22).

In accordance with one embodiment a modified sol-gel composition is provided wherein the peptide-silane composition is selected for optimizing a neuronal phenotype. In one embodiment the sol-gel is modified to include covalently linked peptides comprising a sequence selected form the group consisting of YIGSRSLVRNRR (SEQ ID NO:7), RNNR (SEQ ID NO:5), RGD (SEQ ID NO:1) and CYFQRYLI (SEQ ID NO:6). In one embodiment the peptides are present in a mole ratio of total peptide-silane to silicon dioxide of 0.0025 for both the YIGSR (SEQ ID NO:7) and RGD (SEQ ID NO:1) peptides and at a mole ratio of total peptide-silane to silicon dioxide of 0.025 for the SLVRNRR (SEQ ID NO: 23) and CYFQRYLI (SEQ ID NO:6) peptides. The peptide-silane compositions are then combined with an orthosilicate sol to form a sol-gel comprising covalently linked peptides YIGSRSLVRNRR (SEQ ID NO:7), RNNR (SEQ ID NO:5), RGD (SEQ ID NO:1) and CYFQRYLI (SEQ ID NO:6).

In accordance with one embodiment a nano-textured sol-gel-based hybrid material is provided comprising at least one peptide-silane complex bound to a silica thin film and a population of cells. In a further embodiment nano-textured sol-gel-based hybrid material is provided that comprises multiple sol-gel layers on a substrate. The resulting layers may differ from one another based on the pore size of the sol-gel (i.e., fiber density) or by the peptides that are presented by each layer (either in terms of types of peptides presented or the relative quantity of one or more of the peptides).

Example 1

Use of X-Ray Photoelectron Spectroscopy to Analyze Sol-Gel Surfaces

Chemical surface characterization of biologically modified sol-gel derived silica is an important factor in designing appropriate surfaces for cell substrates, but is somewhat limited. For example, Attenuated Total Reflection Fourier Transform Infrared (ATR FT-IR) spectrometry has been used but is challenging due to the large peak derived from the Si—O bonds, typically covering up the fingerprint region of many organic molecules. Alternatively, atomic force microscopy can provide information on the material topography and can give limited chemical interaction information via phase interactions. Electron microscopy gives structural information and limited chemical information as well. However, the presentation of peptides at the surface of materials requires a precise technique to analyze the chemical nature of the surface of the material for available surface chemistry for critical cellular interactions, such as integrin receptor binding. Such precise characterization of biologically modified sol-gel derived silica has been unobtainable with these analytical techniques.

As demonstrated herein, X-ray Photoelectron Spectroscopy (XPS) analysis can be used to provide a detailed analysis of the surface of peptide modified silica sol-gel derived materials. XPS is a surface sensitive technique that has become widely used for studying properties of atoms, molecules, solids, and surfaces. Generally speaking, intensities of core level photoelectron peaks are used for quantitative analysis, and binding energies of core level photoelectrons exhibit chemically induced shifts. The main success of the XPS technique is associated with studies of the physical and chemical phenomena on the surface of solids. These investigations were limited to relatively simple inorganic reactions and few biologically-relevant problems have been approached using XPS.

Impartial reasons exist for the low involvement of XPS into investigations of biologically-related objects. First, organic chemistry samples often exhibit high vapor pressure and therefore, degas poorly in vacuum creating incompatibilities with the XPS technique. Second, X-rays might cause radioactive damage of a sample. Third, the C 1s region, which is most informative for organic chemistry samples, is narrow and the photoemission peaks can over-crowd the region. At this point NMR and mass spectrometry provide better data on the chemical composition and molecule structure.

The real advantage of XPS, however, is in the study of surface chemistry, and therefore XPS is a potential technique for the characterization of biologically modified sol-gel surfaces. As reported herein, XPS was used to characterize four free peptide-silanes and peptide-silane derived organically modified silica thin films. The spectral characteristics of free peptide-silanes and peptide presenting sol-gel surfaces were compared. Coverage and thickness of peptide-silane layer were calculated. This work demonstrates a use for XPS to characterized biologically-inspired surfaces, providing critical information on peptide coverage on the surface of the materials.

Experimental Section
Reagents and Materials

All Fmoc-protected amino acids, synthesis resin, and O-Benzotriazole-N,N,N',N'-tetramethyl-uronium-hexafluoro-phosphate (HBTU) were purchased from Anaspec, Inc. Tetramethylorthosilicate (TMOS) and 3-aminopropyltrimethoxysilane (APTMS) were obtained from Fluka (Sigma Aldrich). All solvents and remaining peptide synthesis chemicals were obtained from Sigma.

Peptide-Silane Synthesis

Free peptides and conjugated peptide silanes were prepared as described in Example 2. Peptides were purified using ether precipitation, followed by at least 5 ether washes prior to peptide drying, to remove a majority of the protective groups from the peptide-silanes prior to sol-gel synthesis.

Sol-Gel Synthesis

Tetramethylorthosilicate (3.8 mL) (TMOS) was hydrolyzed under acid catalysis with 850 µL purified H2O (18 MΩ) and 55 µL 0.04 N HCl. The sol was then filtered through a 0.2 µm Whatman filter and aged overnight at 4° C. to ensure near complete hydrolysis. Peptide-silanes were solubilized in 0.02 M phosphate buffer (pH 6.0) by sonication at a molar ratio of 0.1% to silicon dioxide. TMOS sol was combined with the buffer containing peptide-silanes at a 30:70 ratio, with an additional 10% of the final volume of methanol added to slow condensation. Thin films were dipped onto piranha-cleaned (sulfuric acid:H2O2, 4:1) WPI coverglass at a rate of 35 mm/second. The peptide silica films were briefly allowed to gel, and then transferred to a closed container in the dry state to reduce surface contamination.

X-Ray Photoelectron Spectroscopy

XPS data were obtained by a Kratos Ultra DLD spectrometer using monochromatic Al Kα radiation (hv=1486.58 eV). The survey and high-resolution spectra were collected at fixed analyzer pass energy of 160 and 20 eV, respectively. The spectra were collected at 0° and 60° angle in the respect to the surface normal. The atomic concentrations of the chemical elements in the near-surface region were estimated after the subtraction of a Shirley type background, taking into account the corresponding Scofield atomic sensitivity factors and inelastic mean free pass (IMFP) of photoelectrons as a standard procedure of CasaXPS software. The peak areas without the IMFP correction were used in Eqs. 1 and 3 because IMFP attenuation is included in the formulas. The binding energy (BE) values referred to the Fermi level were corrected using the C 1s 284.80 eV; the standard deviation of the peak position associated with the calibration procedure was ±0.05 eV. A commercial Kratos charge neutralizer was used to achieve a resolution of 1.0-1.2 eV measured as a Full Width at Half Maximum (FWHM) of the C 1s deconvoluted peaks. The XPS spectra were fitted by CasaXPS software assuming line shape to be a Gaussian-Lorentzian function. No X-ray damage of the samples was detected: the spectra did not degrade with time under X-ray beam and the sample color was also unchanged.

Results

Free Peptide-Silane Analysis and XPS Peak Curve-Fitting Procedure

Before characterization of the peptide thin film surface, free peptides were investigated to determine reference data and to validate the XPS approach and analysis. Four different free peptide-silanes, RGD, NID, KDI and YIG were characterized by XPS. The structures of the peptides are shown in FIG. 1. Peptides were prepared as described in the Experimental Section. Fluoride, oxygen, carbon, silicon, and sulfur were detected by XPS on the surfaces of all samples. Fluoride is an impurity derived from trifluoroacetic acid cleavage, and its trace amounts remain in the peptide-silane post-synthesis and after purification. Complete removal of this impurity would require lyophilization from water or acetic acid post ether purification.

The peptide molecules consist of oxygen, nitrogen and carbon. The O 1s spectra typically show a broad featureless peak of ~1.6 eV FWHM at ~531.5 eV with a high BE shoulder. The N 1s peak is usually at ~400 eV and is also featureless. The C 1s peak is the most promising for XPS characterization. The shape of the C 1s should vary depending on the free peptide-silane structure. As can be seen in FIG. 1, carbon atoms in the peptide structure can be in one of six chemical environments. The first type of carbon is bonded only to carbon and/or hydrogen. The second type of carbon is coordinated with one nitrogen atom along with carbon and/or hydrogen atoms. Type 3 is a carbon atom with a single bond to oxygen atom. Type 4 is a carbon from an amide group. Type 5 is a carbon atom from a carboxyl group. Type 6 is carbon coordinating with three nitrogen atoms, as in arginine. The carbon atoms in these six different positions should have different chemical shifts, and the intensity of the individual components should be proportional to the population of the particular carbon type, therefore, different peptide-silanes are predicted to show the C 1s spectrum with different shape. For convenience, the number of carbon atoms in the different position and their expected binding energies (BE) for different peptide-silanes are summarized in Table 2. The characteristic BE of the C 1s peaks observed in this study are summarized in Table 3. The validation of this curve-fitting technique was verified with the free peptide-silane samples.

TABLE 2

The number of carbon atoms in the different position and expected BE range (free peptides/peptide-silanes).

| | C—C Type 1 | C—N Type 2 | C—O Type 3 | O=C—N (amide) Type 4 | O=C—OH (carboxyl) Type 5 | C—N₃ Type 6 |
|---|---|---|---|---|---|---|
| Binding Energy expected, eV | 284.6-285 | 285.5-286.5 | 286.4-287 | 287.4-288.4 | 288.5-289.6 | 289.0-289.5 |
| NID silane | 18 | 12 | — | 13 | 3 | — |
| KDI silane | 20 | 13 | 7 | 12 | 2 | 1 |
| RGD silane | 20 | 13 | 7 | 12 | 2 | 1 |
| YIG free peptide | 18 | 14 | 2 | 9 | 1 | 1 |

TABLE 3

The characteristic C 1s peak positions observed in this study.

| | C—C, eV | C—N, eV | C—O, eV | O=C—N, eV | O=C—OH, eV | C—$N_3$, eV |
|---|---|---|---|---|---|---|
| Peptide | 284.75 ± 0.04 | 286.16 ± 0.09 | 286.16 ± 0.09 | 288.05 ± 0.13 | 288.75 ± 0.22 | 289.54 ± 0.24 |
| Peptide silane | 284.74 ± 0.07 | 286.33 ± 0.32 | 286.33 ± 0.32 | 288.19 ± 0.36 | 289.17 ± 0.40 | 289.63 ± 0.59 |

The C 1s peak obtained from the free RGD peptide-silane at 0° collection angle was obtained and subjected to curve-fitting analysis according to the technique described above. The relative ratio between six C 1s components was fixed according to the number of the corresponding atoms in the certain peptide structure. It should be noted that no angle-dependence was expected and the spectra obtained from the free peptide-silane samples did not change with the collection angle. Extra components were added to the curve-fitting analysis to accommodate the peaks originating from residual hydrocarbons and the CFx species. Also, in order to simplify the curve-fitting, the C—O and C—N components were simulated by one peak. This curve-fitting procedure of the C 1s spectra demonstrated consistent results for all four peptides: RGD, NID, KDI and YIG. The typical level of the residual hydrocarbons was around 10-15% of total carbon signal and the contribution of the CFx species was less than 2%. The fit was further validated by comparison of the expected ratio of oxygen/carbon and nitrogen/carbon with the XPS measured values. The results are represented in Table 4 and one can see that the XPS measurements and the expected values demonstrate remarkably good agreement. Therefore, XPS can be used for reliable characterization of peptide-silanes.

Specifically, the sodium, potassium, and phosphorous are all components of the phosphate buffer used during the condensation reaction of the sol-gel silica films. The sulfur is a contaminant from dimethyl sulfoxide, used to enhance the solubility of the peptide-silanes. Fluoride is an impurity derived from trifluoroacetic acid cleavage, and trace amounts remain in the peptide-silanes post-synthesis and purification. The K 2p3/2 and K 2p1/2 contributions were added to the curve-fitting profile comparing with the fitting profile for free peptides. The level of residual hydrocarbon was 25-30% of total carbon signal, which is higher than for the free peptide-silanes. Regardless, the surface presented peptides were reliably identified by XPS.

The ratio between nitrogen and carbon calculated from XPS data was close to the ideal ratio for the certain peptide-silane structures as shown in Table 5. Inconsistently high O/C ratio can be explained by oxygen contributions from silica. The curve-fitting analysis resolved two components from the O 1s spectrum obtained from the KDI surface peptide. The high BE component at 532.5 eV is assigned to silica, whereas the low BE peak at ~531 eV is due to peptides. Unfortunately, the strong broad feature of silica oxygen result in poor fitting

TABLE 4

Oxygen to carbon and nitrogen to carbon ratios measured by XPS and expected from the peptide structure.

| | Total carbon amount at % | $C_{peptide}$ amount at % | N amount at % | O amount at % | Ratio between N and $C_{peptide}$ Ideal/XPS | Radio between O and $C_{peptide}$ Ideal/XPS |
|---|---|---|---|---|---|---|
| NID silane | 52.4 ± 0.1 | 41.9 ± 0.3 | 14.1 ± 0.0 | 22.7 ± 0.1 | 0310/0.337 ± 0.0029 | 0.429/0.403 ± 0.0047 |
| KDI silane | 58.3 | 51.8 | 13.7 | 20.7 | 0.278/0.265 | 0.333/0.335 |
| RGD silane | 53.5.0 ± 0.2 | 50.6 ± 0.1 | 14.6 ± 0.0 | 25.3 ± 0.2 | 0.313/0.289 ± 0.00019 | 0.375/0.440 ± 0.0087 |
| YAVTGRGDSPAS free peptide (SEQ ID NO: 11) | 48.2.0 ± 1.3 | 43.0 ± 1.5 | 13.0 ± 0.3 | 25.1 ± 0.7 | 0.291/0.304 ± 0.0032 | 0.400/0.473 ± 0.032 |
| YIG free peptide | 56.6 ± 4.8 | 37.4 ± 0.8 | 21.7 ± 1.0 | 11.4 ± 1.1 | 0.31/0.306 ± 0.036 | 0.333/0.456 ± 0.1856 |

XPS characterization of the peptide thin film surface: The next step was XPS identification of the RGD, NID, KDI and YIG thin-film bound peptide-silanes, which were produced using 1 mole % final peptide-silane concentration to silicon. XPS detected the presence of sodium, fluoride, oxygen, carbon, phosphorus, silicon, sulfur, and potassium on the surfaces of all samples. Sodium, potassium, phosphorous and sulfur are all byproducts of TMOS thin film preparation.

of peptide component and this causes inconsistency in O/C ratio. To verify the surface nature of peptide, the XPS data were acquired at the collection angle of 60° in respect to the surface normal. The data collected at 60° are more surface sensitive, whereas at 0° angle the bulk contribution dominates. As shown by this experiment, the concentration of carbon increases with the angle indicating the presence of peptide at the surface. A short sputtering by Ar+ also resulted in the disappearing of peptide features. This also indicates that peptides are surface species.

TABLE 5

Oxygen to carbon and nitrogen to carbon ratios measured by XPS and expected from the surface peptide-silane structure.

| | Total carbon amount at % | $C_{peptide}$ amount at % | N amount at % | O amount at % | Ratio between N and $C_{peptide}$ Ideal/XPS | Radio between O and $C_{peptide}$ Ideal/XPS |
|---|---|---|---|---|---|---|
| NID silane | 10.2 | 5.3 | 1.3 | 61.2 | 0.29/0.30 | 0.48/1.15 |
| KDI silane | 17.7 | 11.1 | 3.0 | 53.1 | 0.26/0.27 | 0.38/0.54 |
| RGD silane | 19.0 ± 1.6 | 10.8 ± 1.4 | 3.5 ± 0.4 | 51.3 ± 2.6 | 0.31/0.32 ± 0.01 | 0.42/0.23 ± 0.05 |
| YIG silane | 13.3.0 ± 0.4 | 6.2 ± 0.4 | 1.5 ± 0.1 | 58.7 ± 0.3 | 0.29/0.24 ± 0.03 | 0.33/0.18 ± 0.03 |

Discussion

Many factors could potentially affect the surface presentation of the peptides. First, upon thin film formation, the pores of the silica collapse resulting in remarkably different nanoscale morphology comparing to traditional silica monoliths. This collapse will likely affect the presentation of the surface peptides. In addition, surface integrated peptides could interact with one another, increasing the local concentration of peptides in the final material. Finally, sample degradation and chemical contamination on the surface of the materials could potentially occur; altering the final presentation of surface presented peptides. Peptide-silane concentration and structure can alter the final fate of cells existing at the material interface. Understanding how the peptide-silanes present on the surface of thin film peptide-silane materials is important in designing biointerfaces to modulate cellular processes.

Determining the impact of each of the above factors on surface presentation, therefore, is important in the final design of peptide functionalized sol-gels for cell-based devices. The ability of XPS to analyze chemical bonding profiles through binding energy changes can detect peptide degradation and surface presentation of intact peptide-silanes, as well as the presence of chemical contamination. As described herein, XPS can be used for quantification of surface peptide-silanes and for understanding the nature of their surface presentation. Carbon and nitrogen can serve as fingerprints of the surface peptides, whereas oxygen is not a good choice due to a strong signal from the silica sol-gel matrix. The thickness of the peptide layer can be estimated using the intensity of the C 1s and N 1s peaks through the equation:

$$\frac{I_{A,k}}{I^0_{A,k}} = 1 - \exp\left(-\frac{d}{\lambda_{A,k}\cos\theta}\right) \quad (1)$$

where $I_{A,k}$ is the intensity (area) of the k electron level peak (1s) of atom A (in our case carbon or nitrogen) from a certain layer thickness; $I^0_{A,k}$ is the intensity from an "infinitely" thick layer; d is the thickness of the layers in Å; $\lambda_{A,k}$ is the inelastic mean free pass (IMFP) of the photoelectrons emitted from the k level inside of the covering layer in Å; and θ is the take-off angle, which is between the surface normal and the central axis of the electron optics (direction of photoemission collection). In our case, θ was 0° and 60°. The value of $I^0_{A,k}$ ($I^0_{C1s\ I}$ and $I^0_{N1s\ I}$) can be obtained from the free peptide measurements assuming the same roughness for the powder samples and surface peptide thin films.

In order to calculate IMFP, $\lambda_{A,k}$, in polymer compounds the following equation was used:

$$\lambda_{A,k}(nm) = \frac{3.117 \times {}^0\chi^{(v)} + 0.4207 \times N_{rings}}{N_{non-H}} + 1.104 \times \left(E^{A,k}_{kin}(keV)\right)^{0.79} \quad (2)$$

$N_{rings}$ is the number of aromatic six-member rings in the molecule or polymer repeat unit considered, ${}^0\chi^{(v)}$ is the zeroth-order valence connectivity index of Kier and Hall (evaluated by Bicerano's method in the case of a polymer) and $N_{non-H}$ is the number of atoms in the molecule or polymer repeat unit, excluding hydrogen atoms, $E^{A,k}_{kin}$ is the kinetic energy of photoelectrons emitted from the k level. The procedure for calculating ${}^0\chi^{(v)}$ index is given in Cumpson, P. J. Surface and Interface Analysis 2001, 31, 23.

To calculate the thickness of the peptide layer IMFP and $\lambda_{A,k}$ values were used. The results are summarized in Table 6. Total C 1s intensity was used for the calculation without subtraction of residual carbon contributions.

TABLE 6

Peptide coverage and peptide layer thickness.

| | Height, A | | Coverage, Molecules per Si atoms on the surface | |
|---|---|---|---|---|
| | from C 1 s | from N 1 s | from C 1 s | from N 1 s |
| NID silane | 10.3 ± 1.9 | 4.0 ± 0.7 | 0.08 | 0.05 |
| KDI silane | 29.9 | 16.8 | 0.14 | 0.13 |
| RGD silane | 15.0 ± 0.9 | 3.7 ± 0.3 | 0.14 ± 0.02 | 0.14 ± 0.02 |
| YIG silane | 23.2 ± 0.5 | 12.6 ± 1.0 | 0.07 ± 0.01 | 0.06 ± 0.01 |

The error represents the standard deviation obtained by averaging through a few samples.

Peptide coverage is also valuable information, which can be extracted from the XPS data. The intensities of C 1s/N 1s and Si 2p can be used to calculate peptide coverage. The thickness of peptide layers measured using the C 1s peak varies from 10 Å to 30 Å depending on the peptide (Table 6). According to NIST SRD-82, (NIST ElectronEffective-Attenuation-Length Database, SRD-82; version 1.1 ed.; National Institute of Standards and Technology: Gaithersburg, Md. 20899, USA, 2003) 10 Å and 30 Å layers attenuate the substrate signal to 75% and 40%, respectively. These attenuations are within the boundary region between non-attenuating adlayer and attenuating adlayer approximations. Coverages were calculated using the non-attenuating adlayer approximation because (i) adsorbed layers should not be dense and therefore the apparent attenuation should be less than one predicted by NIST SRD-82,41 (ii) the solution for the non-attenuating adlayer approximation is analytical. This approach was verified with a number of adsorption systems, for instance, such as a self assembled monolayers on Au, GaAs, InP, GaP, etc. surfaces. Fadley (Electron Spectrosc.: Theory, Tech. Appl. 1978, 2, 1) proposed that for non-attenuating adlayer approximation the intensity overlayer/substrate ratio can be described as $$\frac{N_l(\theta)}{N_k(\theta)} = \frac{\Omega_0(E_l) \times A_0(E_l) \times D_0(E_l) \times \frac{d\sigma_l}{d\Omega} \times d}{\Omega_0(E_k) \times A_0(E_k) \times D_0(E_k) \times \frac{d\sigma_k}{d\Omega} \times \Lambda_e^{subst}(E_k)\cos\theta} \times \left(\frac{S_{overl}}{S_{subst}}\right). \quad (3)$$

where $N_l(\theta)$ and $N_k(\theta)$ are the peak intensity of the overlayer and substrate, respectively; $\Omega_0$ is the acceptance solid angle of the electron analyzer; $A_0$ the effective area of specimen over which $\Omega_0 \neq 0$; $D_0$ is the instrument detection efficiency, $\theta$ is the angle between surface normal and electron emission direction; $d\sigma_k/d\Omega$ is differential cross-section, which can be calculated using tabulated Scofield cross-sections and the Reilman asymmetric parameter; $\Lambda_e^{subst}(E_k)$ is the IMFP of the substrate photoelectron in the substrate; $S_{overl}$ is the mean surface density of atoms in which peak 1 originates in cm$^{-2}$; $S_{subst}$ is the mean surface density of substrate atoms in cm$^{-2}$; $S_{overl}/S_{subst}$ is the fractional monolayer coverage of the atomic species in which peak 1 originates; d is the mean separation between layers of density s in the substrate.

Eq. (3) was modified and used to estimate the peptide coverages using non-attenuating adlayer approximation, which gives coverage in the modified form:

$$\text{Coverage} = \frac{N_{C_{1s}}}{N_{Si_{2p}}} \frac{\frac{d\sigma_{Si_{2p}}}{d\Omega} \times \Lambda_e^{SiO_2}(KE_{Si_{2p}})\cos\theta}{\frac{d\sigma_{C_{1s}}}{d\Omega} \times d}, \quad (4)$$

where $N_{C_{1s}}$ and $N_{Si_{2p}}$ are the intensity of the C 1s and Si 2p peaks, respectively; $\Lambda_e^{SiO_2}(KE_{Si_{2p}})$ is the IMFP of the Si 2p photoelectron in SiO2; d is the mean distance between the layers of Si atoms in silica. IMFP can be replaced by the electron attenuation length for quantitative analysis, QEAL, and which is calculated by NIST SRD-82 41 to be equal to 33.39 Å. The mean distance d depends on the structure of SiO$_2$ and because the exact structure of substrate is unknown, d was assumed to be equal to 2.5 Å, which is "average" value for the different SiO2 structures. The peptide coverages calculated using Eq. (4) are summarized in Table 6. The values were corrected on the real peptide concentration; the contribution of residual hydrocarbons was subtracted. The coverage is measured in monolayer, ML, which is the ratio between the numbers of peptide molecules and surface silicon atoms.

It should be noted that the surface coverages calculated based on the C 1s and N 1s signals are consistent. The N 1s signal originates exclusively from peptide, whereas the C 1s features of peptide were obtained from the curve-fitting procedure. The consistency between two values unambiguously validates the curve-fitting protocol and also validates the coverage calculations presented by Eq. (4). As seen in Table 6, however, the thickness calculated based on the N 1s peak was much lower than those estimated using the C 1s peak. For instance, the KDI thickness is 29.9 and 16.8 Å as calculated from the C 1s and N 1s peaks, respectively. For the RGD thin film, these values are 15.0 and 3.7 Å (Table 6). Eq. (1) indirectly assumes that the roughness of free peptides and surface peptides is the same. Different surface roughness, however, between the free and surface bound peptides cannot explain the mismatch in the N 1s and C 1s calculations; as this would lead to proportional numerical differences. A variety of morphological and chemical interactions, therefore may be associated with the calculated difference between the N 1s and C 1s peptide thickness.

In addition to the morphology of the thin film structure, several other factors may contribute to the increased peptide concentration and variable molecular height at the surface of the peptide-silane thin films. A primary factor to consider is the likelihood of peptide folding. Each of the peptide-silanes exhibits a variety of chemical characteristics that contribute to hydrophobicity, molecular "bends", and interfacial structure. The nature of peptides to adopt structure based on hydrophobic and electrostatic interactions may also contribute to the conformation of the peptide molecules on the surface.

One can conclude that due to different peptide conformation, N and C are located at different depths in the free peptide and in the surface peptide-silane. Due to peptide folding nitrogen atoms are hidden inside of peptide structure and therefore are closer to the silica surface, while carbon atoms are more exposed. This also implies that peptide configuration is different in the powder form and in the surface state. This conformation potentially explains the larger attenuation of the N 1s electrons compared to the C 1s electrons and results in the apparent lower thickness of nitrogen layer in comparison with carbon layer.

The importance of the peptide conformation can be demonstrated with the following example. As seen in Table 5, the BE of peptide shifts slightly from the expected when the peptide-silane is incorporated into the sol-gel matrix. This shift is very likely due to peptide folding characteristics on the surface of the thin films. Additionally, the NID and RGD peptides have C/N and C/O ratios that are somewhat more skewed from the expected, given the spectral characteristics of the free peptide-silanes. These peptides are of a length sufficient to induce minor secondary structure formation, which can affect both the presentation of particular carbon bonds through masking effects as well as increase the possibility of hydrogen bonding leading to slight BE shifts. This hypothesis is supported by the relatively low measured height of the NID and RGD peptides.

Summary and Conclusions

Four different free peptide-silanes, RGD, NID, KDI and YIG and their thin film were characterized by XPS. This work demonstrates the functionality of XPS to characterize the surface chemistry of biologically inspired sol-gel hybrids. Peptides consisting of oxygen, nitrogen and carbon can be characterized by the O 1s, N 1s and C 1s signals. The N 1s and C 1s peaks were found to be good fingerprints of the peptides, whereas O 1s overlapped with the signal of substrate oxygen and, therefore, the O 1s peak was not informative in the case of the thin films. The N 1s peak originates solely from peptide but the C 1s signal contains also contribution of the residual hydrocarbons, which appeared during sample transfers. In order to separate the contributions of the residual carbon and peptides, the curve-fitting analysis was employed. The peptide constraint was constructed to account for the different chemical states of carbon atoms in the peptide structure. The curve-fitting procedure was validated by analyzing free peptides, RGD, NID, KDI and YIG, in powder forms.

The XPS measured ratios between nitrogen and carbon and between oxygen and carbon were very close to those predicted from the peptide structures. This finding supports the appropriateness of the curve-fitting procedure, which was then applied for thin film studies. The XPS measured ratio between nitrogen and carbon for the peptide thin film was very close to the corresponding value calculated from the peptide structures, whereas XPS ratio between oxygen and carbon was different due to substrate oxygen contribution. The thin films of peptides also contained the residual hydrocarbons in the amount of approximately 30% of total carbon content. The characteristic binding energies are shown in Table 5. The coverage and thickness of the peptide-silane thin films were calculated. The results are shown Table 6. The coverage of the peptide-silanes is in the range of 10% of monolayer (1 monolayer 1ML=the number of presented molecules is equal to the number of substrate atoms). The difference in the peptide film thickness calculated from the N 1s and C 1s peaks was assigned to peptide folding. Based on the chemical structural characteristics of the individual peptides and the experimental XPS data, it can be reasonably assumed that the RGD and NID peptides adopt a globular conformation on the surface of the peptide ormosils, while the YIG and KDI peptides are more linear in nature.

Example 2

Concentration Dependent Surface Presentation of NID Peptide-Silane

Many biomaterial platforms used in mammalian cell culture applications or that are designed for potential biomedical implantable devices have exploited bioactive peptides or extracellular matrix proteins to enhance cell adhesion or direct cell differentiation. One difficulty surrounding this approach is the ability to express biomolecules at biologically relevant concentrations. The cause for this is multi-fold, with the most common issues being a lack of biological data supporting definite concentrations and material preparation techniques.

Current peptide-based materials are generally based on self-assembly chemistry, which requires several steps to complete. This several-step approach is reliant upon critical atmospheric conditions and can easily be hindered by undesirable conditions. These complications often lead to inconsistent surface chemistry between samples, potentially introducing unwanted differences between supposedly identical material samples. While for many experimental applications and studies, this approach is convenient and sufficient, for biomaterials designed for cell culture applications and implantable devices, consistency and concentration regulation of material surfaces is critical. Biomolecule concentration differences less than an order of magnitude may lead to largely different experimental results. Additionally, the need to perform surface chemistry analysis on each implantable device or cell culture substrate is time consuming, expensive, and wholly inconvenient, if not impossible for manufacturers. Therefore, a consistent materials synthesis paradigm provided by the peptide-ormosil platform may therefore offer increased benefit over traditional methods.

Numerous cellular processes operate under concentration or gradient-based interactions. Cell differentiation is dependent upon several factors, including spatial and temporal expression, as well as biochemical concentration. Molecular cues present in the developing cellular system are specific in their expression basis, and the concentrations are critical for the overall appropriate differentiation of the cell. Current methods used in surface modification do not offer the necessary stability or potency necessary to drive a cell line. The peptide-ormosil system may offer increased benefit over traditional cell culture substrates, as it can be designed to interact with specific cell receptors, depending upon the peptide ligands chosen; subsequently activating downstream cell signaling pathways. To direct differentiation of a cell population, the various signaling molecules must be present, at the appropriate concentration, and in a bioactive conformation. The peptide-ormosil platform has been shown to present cellular ligands at the surface through the peptide modifications, however, concentration dependent expression at the surface was not examined.

Experimental Methods
Peptide-Silane Synthesis

Peptide-silanes were synthesized as described above. Briefly, peptides were prepared on Wang resin using standard HBTU (O-Benzotriazole-N,N,N',N'-tetramethyl-uronium-hexafluoro-phosphate) chemistry on an Intavis Multi-Pep automated synthesizer. The resin bound peptides were then conjugated to 3-(aminopropyl) trimethoxysilane (APTMS) in a dry nitrogen environment using 1,1'-Carbonyldiimidazole as a cross linker to the free N-terminus, resulting in the peptide-silane. The peptide-silanes were then cleaved from the resin with trifluoroacetic acid and crudely purified with repeated ether precipitations prior to use. The NID Peptide-silane was chosen as an example to demonstrate concentration dependent surface presentation.

Sol-Gel Synthesis

Silica sol was prepared by hydrolyzing tetramethylorthosilicate (3.8 mL) (TMOS) was under acid-based conditions with 850 µL purified $H_2O$ (18 MΩ) and 55 µL 0.04 N HCl. The homogenous sol was then filtered through a 0.2 µm Whatman filter and aged overnight at 4° C. Peptide-silanes were solubilized by first suspending in 100 µL of dimethyl-sulfoxide (DMSO), and then adding this suspension to 0.02 M phosphate buffer (pH 6.0), followed by brief sonication. The peptide-silanes were then combined with TMOS sol and 0.02 M pH 6.0 phosphate buffer at the desired molar ratios to reach a final TMOS sol concentration of 30%. An additional 10% of the final volume of methanol added to slow condensation. Thin films were dipped onto clean glass coverslips at 35 mm/second. The peptide-silica films were briefly allowed to gel, and then transferred to a closed container in the dry state. The films were used within 24 hours after synthesis.

X-Ray Photoelectron Spectroscopy

XPS spectra of the peptide-silica films were obtained using the methods described in Example 1, above. The NID peptide-silane was chosen as an example.

Results and Discussion

Figure 2A:
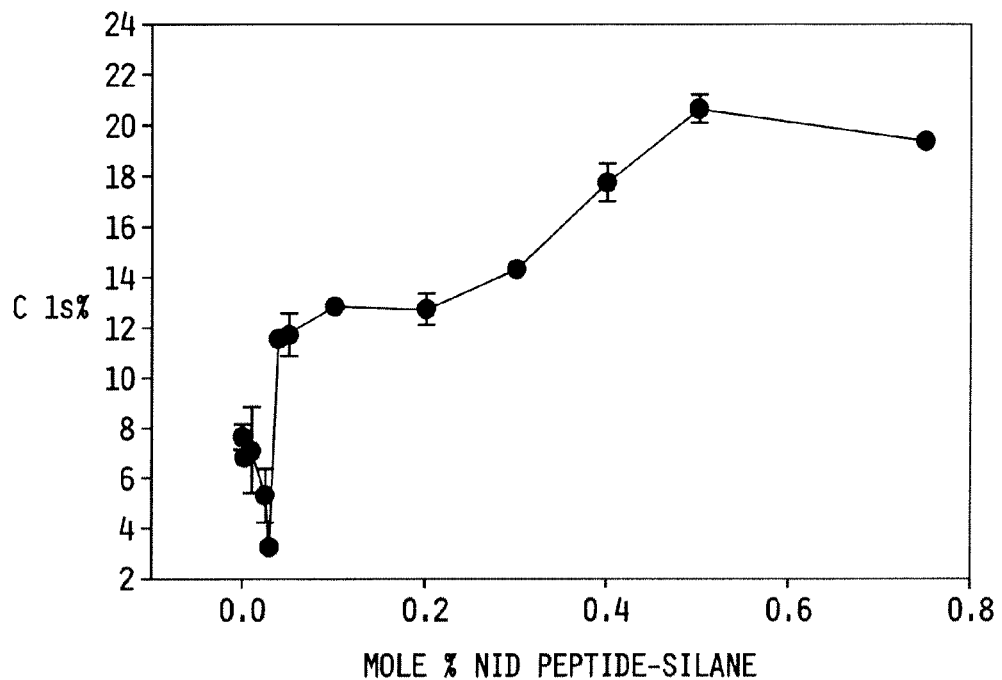
FIGS. 2A & 2B represent the XPS spectra of an NID peptide-silica film prepared in accordance with the present disclosure. The carbon (FIG. 2A) and the nitrogen (FIG. 2B) elemental percentages are shown at the zero degree collection angle using the methods described in Example 1.
Figure 2B:
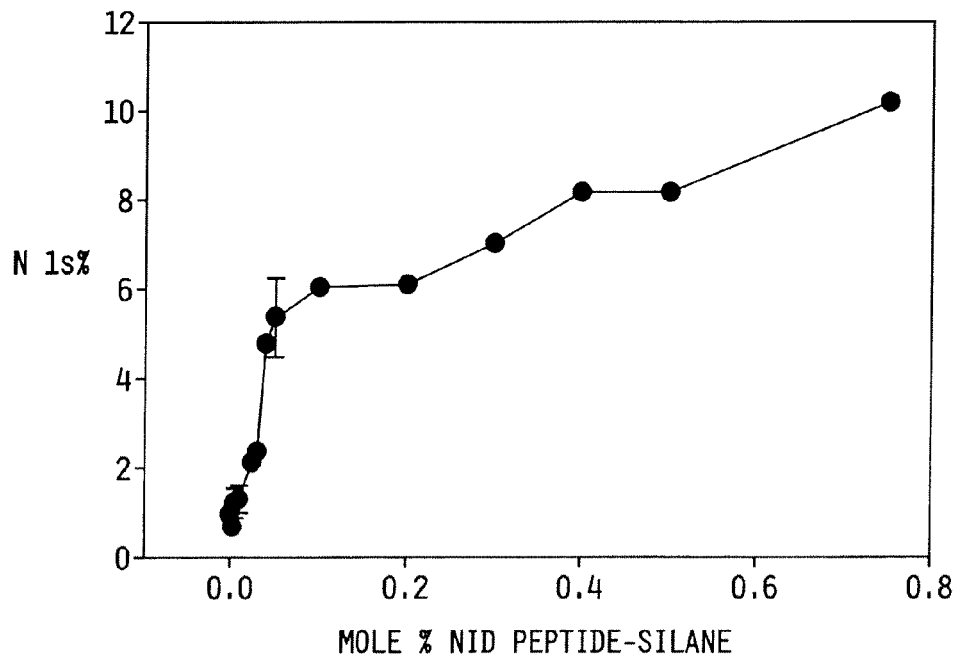

The NID bioactive peptide-silanes were incorporated into a silica thin film at various concentrations to determine if the peptide surface presentation was concentration dependent. The peptide-silane, ANDNIDPNAVAA, simply denoted "NID", appears to follow a hyperbolic surface saturation curve with respect to both the C 1s and N 1s elemental percentages. Both the carbon and the nitrogen elemental percentages are shown below at the zero degree collection angle. At the zero degree collection angle, more bulk properties of the material are examined, and there appears to be some biochemical structural changes occurring at low concentrations, however, the amount of peptide at the surface does not become significant until reaching 0.05 mole % (See FIGS. 2A & 2B).

Figure 3A:
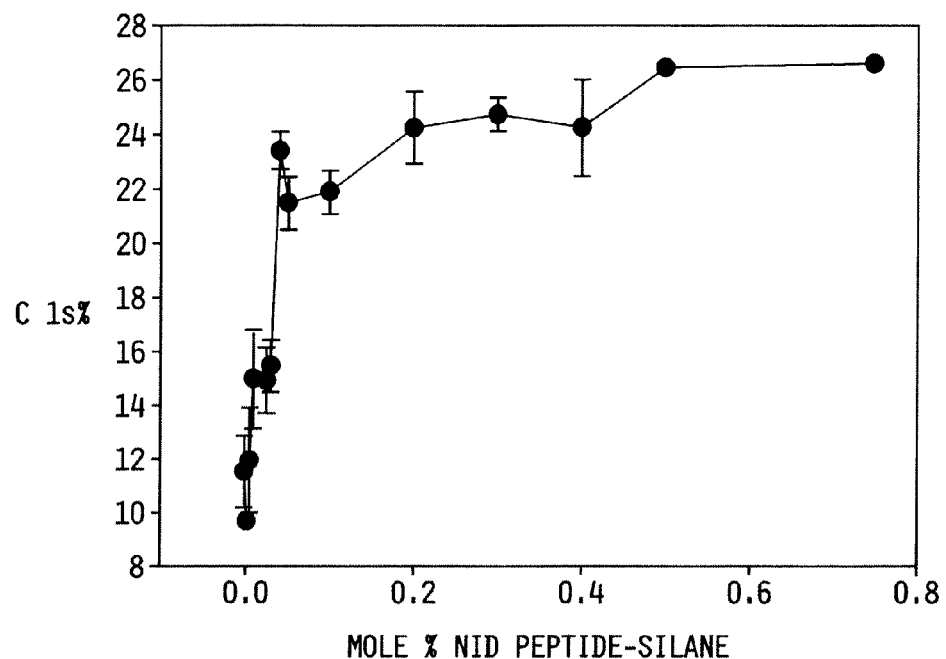
FIGS. 3A & 3B represent the XPS spectra of an NID peptide-silica film prepared in accordance with the present disclosure. The carbon (FIG. 3A) and the nitrogen (FIG. 3B) elemental percentages are shown at the sixty degree collection angle using the methods described in Example 1.
Figure 3B:
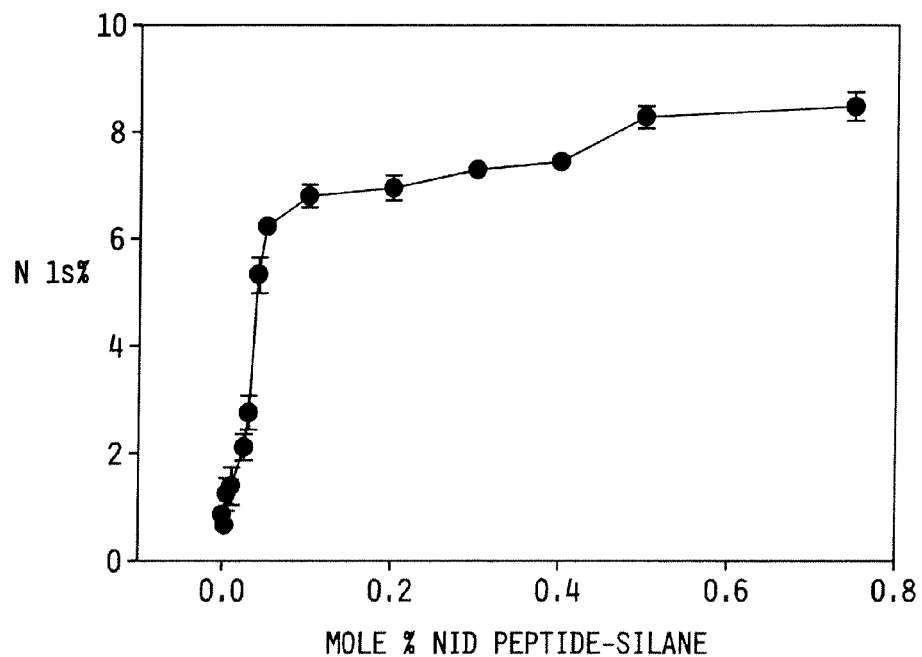

To ensure surface presentation, the concentration dependence was also examined at a 60 degree collection angle (See FIGS. 3A & 3B). The hyperbolic profile persists, and the elemental percentages are slightly increased, leading to the conclusion that the peptides are available at the surface of the silica thin films. The peptide-silanes appear to saturate the surface above 0.5 mole %. While this molar ratio to silicon dioxide seems somewhat low for a saturation profile, it is likely that the peptides are interacting with one another and potentially lying parallel to the surface. The surfaces were not specifically designed to present an ordered peptide profile, therefore, the saturation concentration can reasonably be assumed to be low. Molecules will not necessarily order themselves into a monolayer-type brush pattern, as seen in self assembled monolayer research; therefore, the peptides are not likely in similar conformations with respect to the surface itself. The peptides are designed to fold, however, thus any secondary structure many decrease the apparent carbon detected at the surface, if the peptides are folded in a structure that is deeper than the depth of surface sensitive XPS analysis.

Figure 4A:
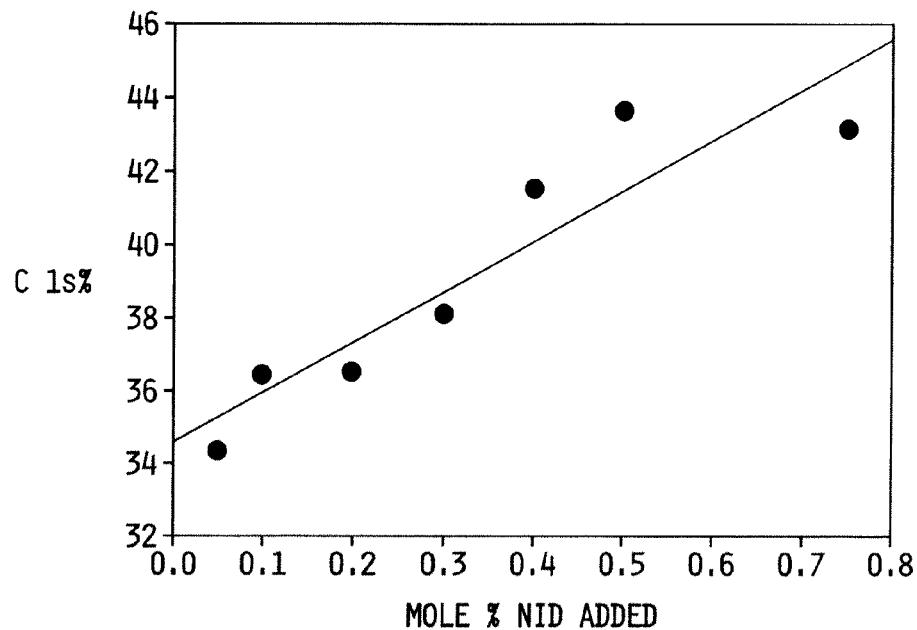
FIGS. 4A & 4B represent a portion of the XPS spectra of an NID peptide-silica film prepared in accordance with the present disclosure. The data demonstrate that within the calibration curves a linear region can be observed over a wide range of mole percentages of starting precursors. Both the carbon (FIG. 4A) and the nitrogen (FIG. 4B) elemental percentages are shown.
Figure 4B:
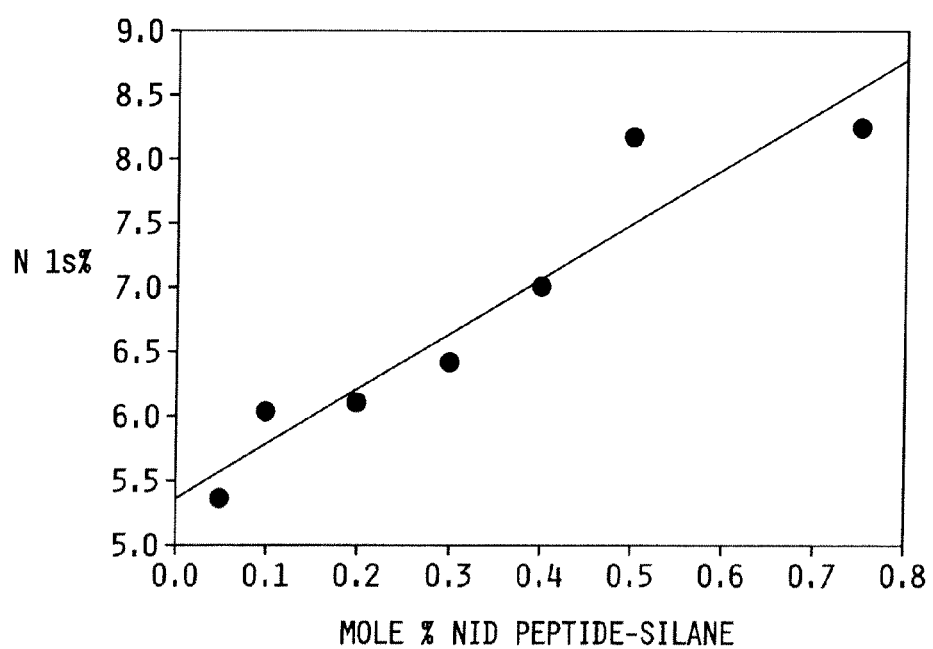

Within the calibration curves a linear region can be observed over a wide range of mole percentages of starting precursors (See FIGS. 4A & 4B).

Conclusions

To conclude, the NID peptide demonstrates a linearized surface presentation dependence upon concentration. The peptide surface concentration can be maintained through simple rational addition of the peptide-silane precursor.

Example 3

Peptide-Silane Sol-Gels as Cell Substrates

In vivo, neural stem cells are confined to localized regions, or niches, where rich extracellular biological cues contribute to the maintenance, proliferation, and commitment of these cells. During development, these cues help to guide cells down specialization paths to mature phenotypes. While knowledge of stem cell niches is far from complete, current research suggests that extracellular proteins contribute in synergistic and concentration dependent ways.

Biologically rich but well-defined, in vitro environments will be important tools for the development of neural stem cell technologies and therapeutics. Surfaces presenting peptide sequences from extracellular matrix and cell-cell adhesion proteins can modulate cell fate and function. Many biomaterial studies implementing peptide chemistry have been based on peptide amphiphiles and self-assembled monolayers. Such materials are powerful model systems and excellent biomimetics; however a lack of stability over time and at air and organic solvent interfaces currently limits this approach for some applications. As described herein, a sol-gel based peptide material was investigated as a potential alternative to self-assembled systems.

The sol-gel method of producing organically modified silica (ormosil) provides a particularly attractive platform for creating biological functionality, as the materials can be doped with a wide variety of organic polymers, biological molecules, biomolecular structures, and living cells. In addition, covalent modification by manipulation of the starting precursor chemistry is possible. The highly porous network enables the diffusion of small molecules for sensing applicants and also for controlled release. Because the gels do not swell, they are an excellent alternative to hydrogels in applications where the leaching of pore contents cannot be tolerated. The materials are optically transparent allowing for the integration of materials with traditional and emerging cytomic tools such as laser scanning adherent cell cytometers. Both native and polymer doped sol-gel produced silica thin films can support cell attachment and growth when the physiochemical surface properties are permissive. Many applications, however, will require a more specific presentation of biological cues. Defining direction of cell fate and function using a materials approach, therefore, requires a method for presenting multiple peptides and an ability to control each peptide surface concentration independently.

To enable a simple and generic method for expression of multiple peptides at the surface of a material, a single reaction vessel synthetic procedure has been developed as described herein, taking advantage of the ability to form solid-state glasses from liquid silanes using sol-gel reaction chemistry. The technique allows for the production of porous organically modified materials whose surface and pores are decorated by the organic moieties of the starting precursors. Peptides are covalently linked to a silane precursor during synthesis, allowing for the covalent incorporation of these peptides into a silica sol-gel matrix.

Peptide silanes were formed in accordance with the present disclosure by the covalent attachment of 3-aminopropyl)trimethoxysilane-tetramethoxysilane (APTMS), using carbonyldiimidazole (CDI) as a linking molecule. This linkage at the N-terminal end of the growing peptide was the last step in a standard solid-state FMOC peptide synthesis before peptide cleavage from the resin. The linkage and peptide molecular weight was confirmed with MALDI-MS and supported by XPS. Peptide silanes were designed based on known binding sequences of the extracellular matrix proteins, fibronectin, laminin and tenascin. The precursors were used in combination with tetramethoxysilane (TMOS) to produce thin films that were then characterized using atomic force microscopy (AFM) and x-ray photoelectron spectroscopy (XPS). The biological functionality of the films and their ability to modulate the cellular phenotype was confirmed using the embryonic carcinoma stem cell line, P19.

Experimental

Peptide-Silane Synthesis

Peptides were synthesized using standard FMOC solid state synthesis on an Intavis Multi-Pep synthesizer. Wang resin was preloaded with the C-terminal amino acid using dimethylaminopyridine (DMAP) catalyzed esterification (Benoiton, N. L., Chemistry of peptide synthesis. Taylor & Francis: Boca Raton, 2006). Protected amino acids were added to the growing peptide chain with the activating reagent 2-(1H-benzotriazol-1-yl)-1,1,3,3-tetramethyluronium hexafluorophosphate (HBTU), see Fields, et al., Peptide Research 1991, 4, (2), 95-101. Upon the addition of the N-terminal amino acid, the Fmoc group was removed under standard 20% piperidine deprotection conditions. 1,1'-carbonyldiimidazole (CDI) (0.4 M in methylene chloride) was then added to the peptide chain under inert gas to activate the N-terminus amino group. Following activation and washing, 0.4 M aminopropyltrimethoxysilane (APTMS) in methylene chloride was attached to the activated N-terminal, forming a covalent linkage between the peptide N-terminal amine and the APTMS with a C=O spacer. After cleaving all side chain protective groups, the peptide-silanes were ether precipitated and crudely purified prior to use. MALDI-mass spectrometry analysis was used as confirmation efficient silane coupling and expected m/z ratio.

Thin Film Materials Synthesis

The peptide-silanes were dissolved in a 50 μl, drop of dimethylsulfoxide (DMSO), suspended in buffer and added in appropriate molar ratios to 30% tetramethoxysilane (TMOS) acid-hydrolyzed sol in sterile 0.02 M pH 7.4 phosphate buffer, with 10% of the final volume of methanol added to slow gelation. Cleaned glass 8 mm glass coverslips (WPI) were dip-coated into the mixture at a constant rate (35 mm/second) to create films of approximately 100 nm in thickness. Films were briefly disinfected in isopropanol or ethanol prior to use and then soaked in buffer for at least 48 hours to remove any synthesis byproducts and to stabilize the peptides. The peptide-silanes contain short peptide chains (6-14mer), and were designed to limit secondary structure formation on the resin, and no significant degradation or denaturation under the mild alcohol conditions used was observed. For cell culture purposes, the thin-film materials were also sterilized under a UV lamp for a minimum of 16 hours.

X-Ray Photoelectron Spectroscopy

XPS data were obtained by a Kratos Ultra DLD spectrometer equipped with a monochromatic Al Kα radiation (hv=1486.58 eV). A fixed analyzer pass energy of 160 eV was used to collect survey spectra, and a pass energy of 20 eV was used to collect narrow region spectra. Atomic percentages from the spectral data were determined.

Atomic Force Microscopy

Peptide TMOS thin films were imaged in buffer using a fluid cell and a closed-loop atomic force microscope (Asylum Research) operating in AC-mode at a scan rate of 1 Hz. The AFM was used to determine the nanotopographical characteristics. The thin films were prepared using filtered materials (0.2 μm pore size) as described and transferred to a sterile hood. After preparation, materials were quickly attached to a glass window of the fluid cell with waterproof, fast setting resin-based adhesive. After allowing 15-30 seconds to adhere, the samples then were placed in gel purified pH 7.4 phosphate buffer. The gels were rinsed and transferred to clean buffer, to prevent any resin byproducts from interfering with the gel structure. Samples were sealed into the fluid cell, immediately covered with the phosphate buffer, and imaged. For all imaging experiments, 60 μm long SiN bio-lever probes (Olympus) with a 0.027 N/m spring constant were used and Z-series, phase, and amplitude traces and retraces were collected and compared. The probe-tips had an approximate radius of curvature of 40 nm. The 512×512 pixel images were scanned at a rate of 1 Hz. The images were flattened under a first order correction and analyzed for height distributions using Igor Pro software.

Cell Culture

P19 embryonic carcinoma cells were obtained from ATCC (CRL—1825). Cells were routinely cultured in α-MEM (Mediatech) supplemented with 7.5% bovine calf serum (BCS) and 2.5% fetal bovine serum (FBS) (Hyclone). Cells were passaged at 75% confluency or every four days using trypsin EDTA (Hyclone). To induce neuronal differentiation, cells were exposed to 5×10−7 M all-trans retinoic acid (Sigma Aldrich) in α-MEM media supplemented with 0.5% FBS in 10 cm bacteriological grade petri dishes (Falcon) for 5 days. Post-induction, cells were plated on UV-sterilized 8 mm peptide-silane thin films, TMOS thin films, and control tissue culture dishes (Corning) coated with 0.5 mg/mL rat tail collage (Becton Dickinson) at a density of 40,000 cells/cm$^2$. Differentiated cells were fed every two days using a low serum version of the standard media formulation for maintenance of P19 cells. Specifically, the serum concentration was reduced to 1% FBS in α-MEM. Cells were imaged daily to track morphological changes with a Nikon inverted T100 microscope and attached CoolSnap camera. Cell morphology was quantified from the brightfield images using the NeuronJ plugin of ImageJ. Primary neurites were traced from the cell body and converted to micrometers from pixel counts.

Cells were assessed using both flow cytometry and immunofluorescence quantification. Flow cytometrical cell type analysis of the differentiated cell populations were acquired at 8-10 days post-seeding. Cells were detached from the materials using trypsin-EDTA. Following detachment, cells were resuspended in one part 50% FBS in PBS (pH 7.4), and fixed with three parts ice-cold 70% ethanol overnight at 4° C. Fixed cells were then permeabilized for 10 minutes in PBS (pH 7.4) with 0.1% Triton X-100, 1% bovine serum albumin and 1% sodium azide (PBST). Following permeabilization, cells were blocked for one hour at room temperature using PBST supplemented with 10% normal goat serum. Alexa 488 conjugated antibody to beta-tubulin III (Tuj1, Covance) and Cy3 conjugated antibody to glial fibrillary acidic protein (GFAP, Sigma) were used to detect neurons and astrocytes, respectively. The primary antibodies were added to the blocked cells in PBS-T supplemented with 1% NGS, and the cells gently agitated overnight at 4° C., followed by washing three times in PBS-T. The cells were subsequently washed three times and analyzed using a Beckman Coulter Altra Cell Sorter. The percentage of cells positive for the immunochemical markers were averaged over at least four independent cell populations. A students t-test was performed to determine significance of the population differences ($\alpha<0.05$).

In situ immunofluorescence staining and confocal analysis was also performed to confirm the flow cytometric data and brightfield morphological analysis. Briefly, cells were fixed in situ using 4% paraformaldehyde for 15 minutes, followed by washing in PBS-T and permeabilization with 0.1% Triton X-100. Cells were blocked in PBS-T with 10% normal goat serum. Antibodies identical to the flow cytometric protocols were added to the plates following the timing as discussed above. After the final washing, the cells were analyzed using a Bio-Rad Radiance Multiphoton confocal microscope.

Results and Discussion

Peptide Silane Synthesis

Peptide-silanes were synthesized and then characterized using MALDI-MS. The peptide-silanes were compared to free peptides to obtain fractionation characteristics of the precursors of interest. FIG. 1 shows the structures of the four peptide-silanes created. Table 7 provides the sequence of the four unmodified peptides along with their natural source proteins. The four peptides were chosen for their known biological functions in neuronal development. The YIGSR (denoted YIG in data) and RGD peptides are cell binding regions found in the extracellular matrix proteins, fibronectin and laminin, and are commonly employed in biomaterial surfaces to improve cell adhesion and survival on artificial materials. The KDI sequence directs cellular migration, facilitates axon guidance, and enhances the formation of basic neuronal architecture. The NID peptide sequence is a common EGF repeat found in the extracellular matrix proteins, laminin and tenascin, which contribute to the neural stem cell niche within the sub-ventricular zone and modulates the effects of growth factors.

TABLE 7

Peptides chosen for study.

| Peptide Sequence | Name | Origin | Function |
|---|---|---|---|
| AND *NID*PNAVAA SEQ ID NO: 14 | NID | EGF Repeat Laminin, Tenascin | Basement Membrane Organization |
| AYAVTG*RGD*SPASA | RGD | Fibronectin Type | Adhesion, Synapse |

TABLE 7-continued

Peptides chosen for study.

| Peptide Sequence Name | Origin | Function |
|---|---|---|
| SEQ ID NO: 15 | III Repeat | Formation |
| ARDIAEIIKDIGA SEQ ID NO: 16 | KDI Laminin | Migration, Guidance, Neuronal Architecture |
| ADPGYIGSRGAA SEQ ID NO: 17 | YIG Laminin | Adhesion, Synapse Formation |

Peptides were chosen to represent the developing embryonic neural environment. Bolded residue indicate cell binding sequence.

Peptides with a longer sequence length than simply the primary bioactive peptide were used, as they are more likely to mimic the natural conformations found in ECM protein secondary structure. Flanking amino acids were determined from the native protein sequence, and an alanine was added to the C-terminus during synthesis through the use of a preconjugated Wang-Ala resin. In addition a minor modification to the N-terminus by the addition of an alanine improved the overall linkage capability of the CDI/APTMS terminating group.

MALDI-MS was used to characterize the average m/z ratios of the resulting peptidesilanes. The peptides and peptide-silanes were partially purified through multiple ether extractions and subjected to standard MALDI conditions. The free peptides and peptide silanes of each sequence of interest were analyzed for comparison. Many of the peptide-silanes appear to have undergone partial hydrolysis of the APTMS methyl groups. This hydrolysis is expected, given the trifluoroacetic acid conditions used for peptide cleavage from the resin. The molecular ions generated for each sequence product are within experimental limits of the expected nominal molecular mass, demonstrating a successful conjugation of the APTMS with the CDI linker. There are, however, some minor peaks associated with each of the samples that potentially signal the incomplete removal of amino acid protective groups. These artifacts can be removed through a longer TFA treatment and the use of specific scavengers for the protective groups used with the peptide synthesis in future work. Overall, the MALDI-MS data confirms that the peptide is conjugating effectively to the APTMS molecule, and that the peptides themselves are of an expected molecular mass given the chosen sequence. As this technique is developed further for potential therapeutic applications, a more sensitive technique, such as LC-ESI-MS/MS may be applied to confirm peptide sequence and purity.

MALDI-MS was chosen as an analysis technique for these molecules over the traditional silane characterization techniques of nuclear magnetic resonance spectroscopy and Fourier transform infrared spectroscopy (FT-IR) due to the peptide-based nature of the molecular structure and the tendency for hydrolysis under acid cleavage. FT-IR was initially used for basic analysis of the peptides, however, this method could not be used for confirmation of conjugation due to the carbon fingerprint region overlap with the identifying Si—O peak (1000-1100 $cm_{-1}$). Additionally, X-Ray Photoelectron Spectroscopy (XPS) was used for surface analysis of the peptide-silanes; the presence of a silicon peak in the XPS spectra was further indication that the conjugation was successful.

X-Ray Photoelectron Spectroscopy

To confirm the presence of the peptides at the surface of the peptide-silane silica films, X-Ray photoelectron spectroscopy (XPS) was employed to analyze the atomic composition of the peptide-silane thin films (See Example 1). Thin films were prepared as described below, using a final concentration of 0.1 mole % peptide-silane to TMOS derived silica. This ratio, while significantly higher than many of the potential biological ratios that will be used in the future, represents a quantity that is easily detected by XPS. Future work will include calibration curve analysis to determine the lowest surface relevant concentration. XPS spectra were analyzed and deconvoluted to yield atomic percentages present on the surface of the materials. Organic contamination was eliminated from the sample spectrum through mathematical means.

The XPS data revealed the presence of carbon and nitrogen species on the $SiO_2$ surface. To confirm that the carbon and nitrogen peaks were from the peptides, the ratio of N:C was compared to the ideal N:C derived from the expected structure. The structural N:C was obtained by enumerating the carbon and nitrogen atoms in the expected molecular structure. These ratios are within reasonable limits of the ideal N:C, providing reasonable confirmation that the organic species present on the surface of the peptide-derived silica thin films is from the incorporated peptide. The correlation between the ideal N:C based on structural information and the experimental N:C of the non-silicon bound peptide-silanes can also help confirm that the peptide synthesis was successful and that there are not any significant additions or deletions in the peptide sequence.

While it is evident from many of the contaminating species in the spectra, such as sodium and fluoride that the peptide-silanes are not of a purity normally required for peptide studies, the purity of the ormosil surfaces is enhanced through multiple washes of the resultant thin films. This eliminates unwanted atomic species and leftover organics from the synthesis reaction; which could potentially interact negatively with cells. Each of the contaminating species can be attributed directly to synthesis and purification agents; specifically, fluorine byproducts are associated with trifluoroacetic acid cleavage.

In addition to analysis of the surface bound peptide-silanes, XPS analysis was performed on the free peptides and free APTMS conjugated peptides (peptide-silanes). The carbon, nitrogen, and oxygen profiles of the free peptides and peptide-silanes are similar between the samples, with the primary differences occurring in the oxygen and silicon peaks. Of significant importance, the silicon peak is apparent in the silane conjugated peptides, at 2.38%, while there appears to be only background contaminant silicon in the peptide, with a spectral percentage of 0.01%. In addition, the oxygen percentage is considerably larger in the peptide-silane spectra (+5%), which may be attributed to the silane-derived methoxy groups that may still be attached to the molecule. This comparison between the free peptides and peptide-silanes provides additional confirmation of the successful conjugation between the APTMS molecule and peptide chain.

The XPS data indicated the availability of the peptide on the surface of the silica thin films. In addition, it serves as a confirmation of the successful silane conjugation on the amine terminus of the peptide. Given the bulky nature of these molecules, the surface nanotopography may be altered by the addition of peptide quantities at biologically relevant concentrations. To test this theory, AFM was employed to examine the nanotopographical and phase interactions of the thin film ormosils.

Surface Features of the Peptide Ormosils

Previous studies by applicants indicate that the nanostructure of silica sol-gel surfaces plays a fundamental role in neuronal adhesion and survival properties. Specifically, thin-film sol-gel morphology, with height features ranging between 25-100 nm, supports PC12 neuronal adhesion. In contrast, bulk silica monoliths, with features ranging from 100-250 nm, are non-permissive to PC12 neuron adhesion. These adhesion profiles have been determined to be associated with electrostatic and topography-induced patterns of ECM protein unfolding on the various surfaces. The presence of ECM peptides in the materials, however, will likely reduce or alter the effects of nanotopography by providing specific cell binding sites at the surface. To determine the nanotopography of the peptide-silane material surfaces, AFM images were collected of thin films produced from each of the four peptide-silane precursors at mole percentages used in Jedlicka, et al, Journal of Materials Chemistry 2006, 16, (31), 3221-3230. These images principally serve to confirm that the addition of bulky peptide molecules at biologically relevant ratios does not significantly alter the thin film features outside of the range of native thin films. Any changes in cell function on the peptide ormosils are therefore likely due to the peptides themselves and not secondary changes in surface features.

The NID and KDI materials were prepared at a higher mole percentages compared to the basic cell adhesion peptides, YIG and RGD. Both the NID and KDI materials have well defined surface features in the range of 50-75 nm. In addition, a small amount of noise resulted from the tip sticking to the surface indicating tip-material interactions were present. This interaction is not observed in unmodified TMOS films and is likely due to the presence of the peptide.

YIG and RGD were used at extremely low concentrations (0.0025 mole %) based on biological function. Resulting films lack defined features and appear similar to unmodified TMOS derived films. These AFM images, therefore, indicate that surface nanotopography is likely a function of the concentration of peptide at the surface. The nanotopography of the thin film materials is consistent with the morphology observed in TMOS thin films, which are capable of supporting neuronal adhesion. Therefore, it is reasonable to assume that the peptide modified silica films will be able to support cellular adhesion. The larger features apparent on the NID and KDI films are approaching the feature size of bulk gel materials, however, the incorporation of the peptide derived integrin ligands should eliminate any undesired effects on cell adhesion due to feature size by supplying specific cell binding sites. To examine this potential of the materials to support neuronal cells, P19 cells were used as a cellular model.

Cellular Response of Pluripotent P19 Cells

P19 cells are an established model for studying neuronal differentiation and were selected for demonstrating the biological functionality of the peptide ormosils. Established by McBurney in 1982 (see McBurney, M.; Rogers, B., Developmental Biology 1982, 89, (2), 503-508 and McBurney, M. W., International Journal of Developmental Biology 1993, 37, (1), 135-140). P19 cells are a pluripotent embryonic carcinoma cell line with many features of embryonic stem cells. When exposed to retinoic acid (RA) and allowed to aggregate, P19 cells can differentiate into fibroblast-like, glial, and neuronal cells. The ratio of cell types varies with extracellular environment conditions in culture. The resulting neurons can mature to form both inhibitory and excitatory synaptic connections.

The peptide ligands in the material composition were anticipated to impact the differentiated cell composition and neuronal morphology after retinoic acid treatment. Due to the dramatic differences in the morphology and biochemical characterization of neurons compared to astrocytes and fibroblasts, these cell population compositional changes should be observed by microscopy and immunofluorescent techniques. After retinoic acid treatment, cells were plated on thin films containing a combination of the basic adhesion peptides, RGD and YIG, as well as on films containing the three peptides RGD/YIG/NID (see Table 8). Three peptide-silanes in two combinations were explored to explore the potential utility of the peptide-silane thin films. The peptide-silanes were incorporated into the silica thin films using ratios shown. These materials were compared to standard 30% TMOS sol-gel derived silica thin films and collagen coated tissue culture plastic.

TABLE 8

Experimental Materials for Cell Studies.
Material Type

| | TMOS sol | Peptide Silane | Mole % Added |
|---|---|---|---|
| Adhesion Peptides | 30% | RGD | 0.025% |
| | | YIG | 0.025% |
| Adhesion + BM Peptides | 30% | RGD | 0.025% |
| | | YIG | 0.025% |
| | | NID | 0.100% |

TABLE 9

Figure 5:
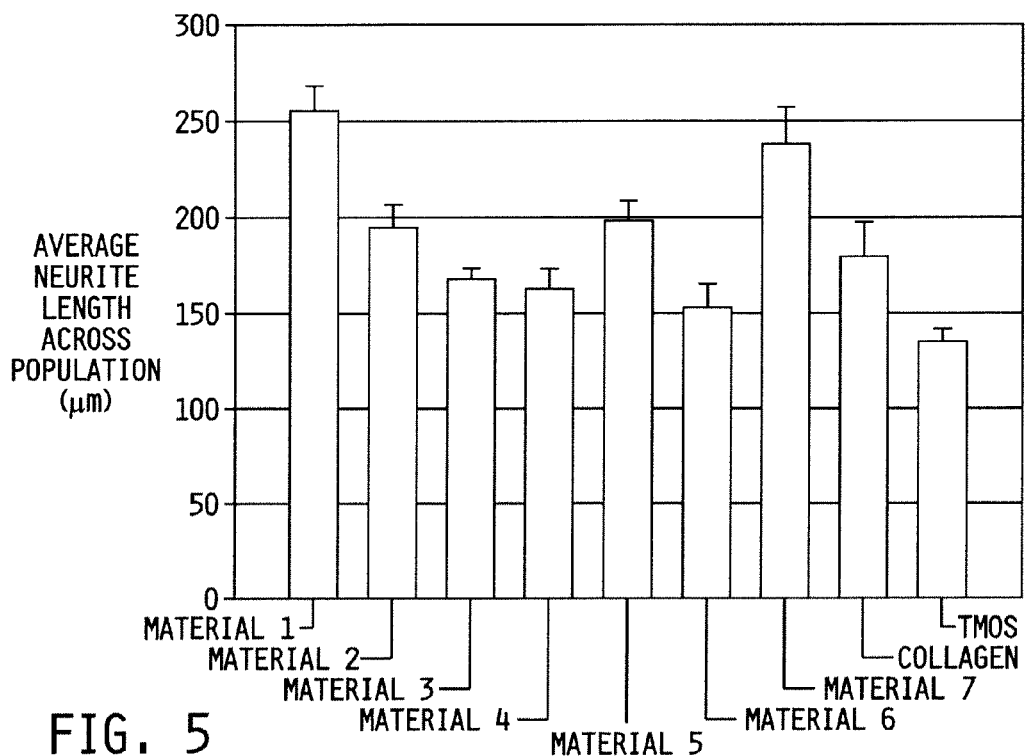
FIG. 5 is a graphic representation of the neurite length analysis of P19 cells cultured on various peptide modified hybrid sol-gel substrates as listed in Table 9. Material 1 containing YAVTGRGDSPAS (SEQ ID NO:11) and DPGYIGSRGA (SEQ ID NO:13) material 2 containing YAVTGRGDSPAS (SEQ ID NO:11), DPGYIGSRGA (SEQ ID NO:13) and ANDNIDPNAVAA (SEQ ID NO:14), material 3 containing YAVTGRGDSPAS (SEQ ID NO:11), DPGYIGSRGA (SEQ ID NO:13) and AASIKVAVSADRG (SEQ ID NO: 21), material 4 containing YAVTGRGDSPAS (SEQ ID NO:11), DPGYIGSRGA (SEQ ID NO:13) and SLVRNRRVITIQG (SEQ ID NO: 22), material 5 containing YAVTGRGDSPAS (SEQ ID NO:11), DPGYIGSRGA (SEQ ID NO:13) AND-NIDPNAVAA (SEQ ID NO:14), AASIKVAVSADRG (SEQ ID NO: 21), VSWFSRHRYSPFAVS (SEQ ID NO: 20), SLVRNRRVITIQG (SEQ ID NO: 22) and CYFQRYLI (SEQ ID NO:6), material 6 containing YAVTGRGDSPAS (SEQ ID NO:11), DPGYIGSRGA (SEQ ID NO:13) AASIKVAVSADRG (SEQ ID NO: 21), VSWFSRHRYSPFAVS (SEQ ID NO: 20), and SLVRNRRVITIQG (SEQ ID NO: 22) and material 7 containing YAVTGRGDSPAS (SEQ ID NO:11), DPGYIGSRGA (SEQ ID NO:13) SLVRNRRVITIQG (SEQ ID NO: 22) and CYFQRYLI (SEQ ID NO:6). Images were collected of live cells at 8-10 days after seeding post-retinoic acid induction. The images were analyzed for neurite length using the NeuronJ plugin for ImageJ. Neurites were traced from the cell body to the terminal end of the primary neurite. Secondary neurites were observed but not quantified in this analysis. ($\alpha<0.05$)
Figure 6:
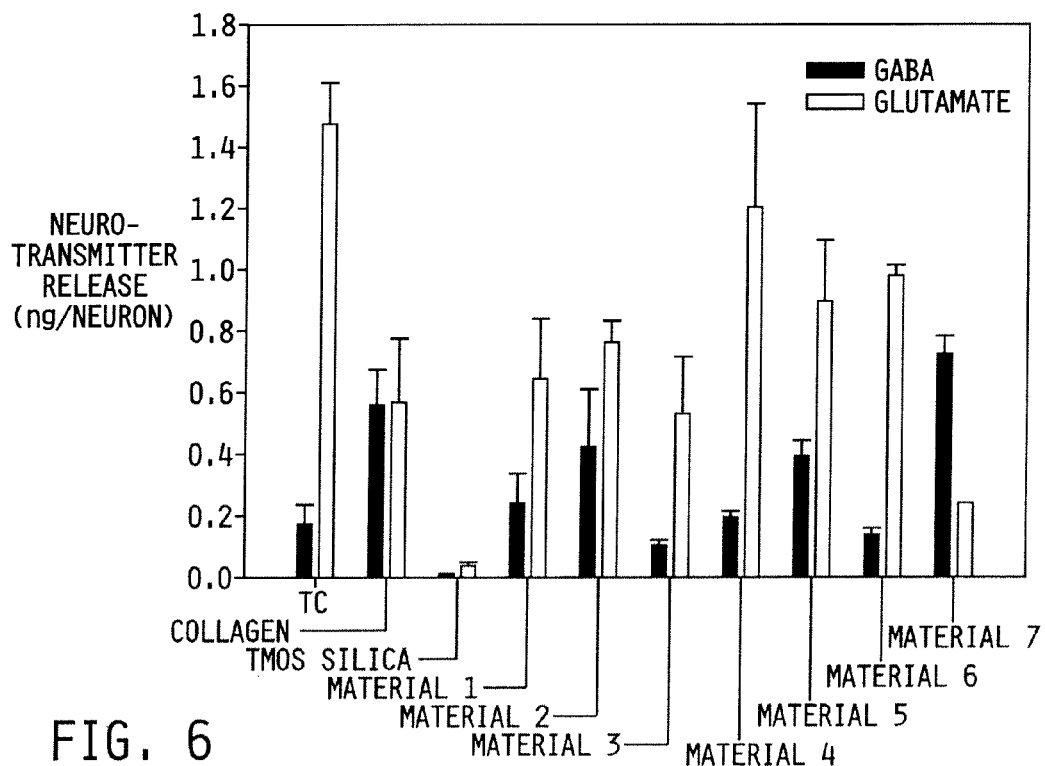
FIG. 6 is a graphic representation of stimulated release of GABA and glutamate from retinoic acid induced P19 cell cultured on one of seven peptide modified sol-gel surfaces (materials 1-7 as defined in FIG. 5 above and in Table 9) as well as three controls in accordance with Example 3. the three control substrate are as follows: 1) tissue culture plastic substrate (TC), Tetramethylorthosilicate (TMOS) sol-gel derived silica thin film, and collagen coated tissue culture plastic substrate (collagen). The amount of GABA and glutamate released by the cells was measured. As the data shows, the material composition of the substrate alters neurotransmitter release of cell populations, wherein supporting peptide signals increase neurotransmitter release. Furthermore, the use of adhesion peptides YIGSR (SEQ ID NO: 7) and RDG (SEQ ID NO: 1) was found to support increased cell diversity relative to either of the two controls (TMOS or collagen substrates).

Peptide-Silane Cell Substrates for FIGS. 5 and 6

| | Mole % Peptide-Silane | | | | | | |
|---|---|---|---|---|---|---|---|
| Material # | A | B | C | D | E | F | G |
| 1 | 0.0025 | 0.0025 | 0 | 0 | 0 | 0 | 0 |
| 2 | 0.0025 | 0.0025 | 0.1 | 0 | 0 | 0 | 0 |
| 3 | 0.0025 | 0.0025 | 0 | 0.0125 | 0.0125 | 0 | 0 |
| 4 | 0.0025 | 0.0025 | 0 | 0 | 0 | 0.025 | 0 |
| 5 | 0.0025 | 0.0025 | 0.1 | 0.0125 | 0.0125 | 0.025 | 0.025 |
| 6 | 0.0025 | 0.0025 | 0 | 0.0125 | 0.0125 | 0.025 | 0 |
| 7 | 0.0025 | 0.0025 | 0 | 0 | 0 | 0.025 | 0.025 |

A = YAVTGRGDSPAS (SEQ ID NO: 11); B = DPGYIGSRGA (SEQ ID NO: 13); C = NDNIDPNAVA (SEQ ID NO: 14); D = AASIKVAVSADRG (SEQ ID NO: 21); E = VSWFSRHRYSPFAVS (SEQ ID NO: 20); F = SLVRNRRVITIQG (SEQ ID NO: 22); G = CYFQRYLI (SEQ ID NO: 6)

The first composition was chosen to determine if the simple addition of two commonly used adhesion peptides to the surfaces of the thin film materials would enhance the utility of silica thin films as a cell culture substrate. The second material was chosen to explore the potential effects of adding a peptide known to play a role in extracellular patterning and basement membrane formation (NID), creating a more "rich" extracellular environment.

The final peptide discussed in this paper (KDI) was not used in cell studies, but will be explored in future work. The primary function of the KDI peptide is neuronal pathfinding and could potentially be useful in spatial cell direction. Based on developmental research, it is well known that many extracellular matrix proteins, specifically fibronectin, only appear in limited amounts during neural stem cell proliferation, differentiation, and migration. Therefore, the fibronectin RGD group was used at a very low molar ratio. The YIG group, known as a neuronal cell adhesion molecule, was also limited in molar ratio for the purposes of this study. As protein quantification in the absolute sense is somewhat elusive, these ratios represent a combination of developmental ratios, primarily based on whole protein analysis, and quantities used in existing peptide-modified biomaterial work.

Cells were plated on the peptide materials and compared to cells on the unmodified TMOS derived thin film and on a collagen coated tissue culture plate control. The cells were maintained on the materials in α-MEM supplemented with 1% FBS to ensure that the cells were interacting with the peptide materials and not a layer of serum proteins. This treatment has also been shown to increase the proportion of neuronal cells in the differentiated population, due to the starvation of non-neuronal and undifferentiated cells. The cellular response to the materials was qualitatively analyzed using standard morphological observation. The unmodified TMOS films result in few neurons. Of noteworthy importance, in the low serum environment, the cells only rarely migrated out of the plated aggregates on the TMOS derived silica.

In contrast, the RGD/YIG films appear to enhance the neuronal morphology of the cells over standard TMOS derived silica thin films. When the NID peptide, known to facilitate extracellular matrix interactions, was included, an increase in neuronal processes per field of view was observed. A network of long cellular processes forms on both peptide modified materials. In addition, both of these peptide ormosils appear to support a wide variety of morphologically-distinct cell types, while the collagen control seems to support a larger proportion of neuronal cells. As these observations are purely based on cell morphology, a quantitative analysis of cell type was conducted.

To analyze the cell type and confirm the morphological observations, several assays were performed. First, confocal analysis of β-tubulin III was performed to examine the neurite patterns of the adherent neuronal cells. The confocal images indicate that while each material type does support neuronal cells, the neurite processes on each of the material types are altered in agreement with the initial morphological observations. On the collagen coated tissue culture control, there are several β-tubulin positive cells in each view, however, the neurite processes of these cells are relatively short. In addition, the lack of nuclei not associated with the neuronal cells demonstrates a lack of supporting glial cells. In contrast, the RGD/YIG and RGD/YIG/NID peptide-silane thin films supported a variety of cells, shown by the density of nuclear staining. The neurite processes on these two material types are also much longer than the collagen control. The RGD/YIG/NID peptide-silane films also seemed to support more neurite processes per field. Overall, the peptide-modified silica films appear to enhance the neuronal maturation of the P19 cells over the collagen control surfaces and native silica films.

As an additional confirmation of the morphological differences of adherent cells, neurite length was quantified using the NeuronJ plugin of Image J 42. Neurites were traced from the cell body and quantified based on pixel conversion to micrometers. At least 5 images were analyzed per experiment, with at least 10 neurite traces performed per image. This data is presented in FIG. 2. The peptide-silane materials supported longer neurite processes, which is likely due to the density of glial cells enhancing the maturation of the adherent neurons. The RGD/YIG, surprisingly, supported longer neurites than the RGD/YIG/NID combination, although the RGD/YIG/NID combination did appear to support more neurite processes per field. The collagen control surfaces do sustain the neuronal population, however, based on neurite length, it can be reasonably deduced that the neuronal cells are less mature than those associated with the peptide ormosil materials. The TMOS derived silica films, as expected, supported the shortest processes.

As an initial examination of the potential of the materials to modulate cell type, FACS analysis was performed to quantify the percentage of neuronal and astrocytic cells in the culture population. Neuronal cells were labeled with AlexaFluor 488 conjugated beta-tubulin III, and astrocytic cells labeled with Cy3 conjugated GFAP. This data is presented in Table 10. Material-exposed P19 embryonic carcinoma cells were grown on the described material types for 8-10 days. Cells were then removed from the materials and subjected to immunocytochemical protocols and FACS analysis. The percentage of cells positive for the various anticipated (GFAP—astrocytic cells, Tuj1—neuronal cells) are presented. The standard error across the experiments is designated by the number within the parenthesis. (*** α<0.05)

TABLE 10

Immunopositive Cell Type Analysis.

|  | TMOS silica | RGD/YIG | RGD/YIG/ NID | Collagen Control |
|---|---|---|---|---|
| Tuj1+ *** | 0.875 (0.325) | 2.86 (0.35) | 5.325 (0.48) | 15.58 (0.82) |
| GFAP+ | 9.625 (1.57) | 9.75 (2.46) | 13.725 (1.23) | 6.9 (0.66) |

The collagen control, as expected, supports the largest percentage of neuronal cells and a smaller percentage of astrocytic "support" cells over the peptide modified silica films. The TMOS derived silica supports very few neurons (0.875%), as well a population of astrocytic cells.

Considering the infrequency with which the cells migrated out of aggregates on the TMOS derived silica, these data are reasonable. The peptide materials, based on cell type analysis, appear to have a significant effect on the cell population. The RGD/YIG "adhesion" material appears to promote a significantly smaller population of neuronal cells than the collagen control and the RGD/YIG/NID composition. In addition, the RGD/YIG/NID composition espouses a larger number of astrocytic cells, which may enhance the ability of neurons to develop, survive, and ultimately mature. Overall, the cell population analysis appears to correlate with the neurite length quantification and confocal analysis of the differentiated P19 cells. The NID peptide is known to be involved in a variety of cellular signals. While the specific pathways that are being modulated cannot be ascertained with certainty, it is evident that the NID peptide does enhance the neuronal population in terms of neuronal percentages over the RGD/YIG material. The numerical count of neurons is less then that on the collagen control surfaces. In addition, given the increased length of neurites and formation of a network of processes on the RGD/YIG/NID surfaces, it is possible that the neurons have reached functional maturity.

The selected peptides used in this study have all been drawn from known integrin interactions in the developing vertebrate nervous system. Integrins are the major class of receptors utilized by cells to interact with ECM protein ligands. Upon ligand binding, integrins cluster on the cell surface at sites termed focal adhesions, leading to the assembly of intracellular multiprotein complexes associated with the cytoskeleton. Focal adhesions, beyond acting as structural links between the ECM and cytoskeleton, are sights of signal transduction from the ECM. The manipulation of P19 population phenotype demonstrates that the incorporated peptides are available to the receptors at the cell surface and the peptide precursors are able to impart biological functionality into the sol-gel thin films.

CONCLUSION

A method for the synthesis of chemically conjugated peptides to silane precursors has been provided. These precursors can then be added at particular mole percentages to standard TMOS derived silica thin films during condensation to improve the biological compatibility and ultimately neuronal differentiation patterns of P19 embryonic carcinoma cells. Through the use of selected cellular interactions, the identity and maturity of the experimental cells can be modified.

Previous work by many groups have focused on the facilitation of neuronal growth through the use of biomaterials modified with extracellular matrix (ECM) components such as immunoglobulin, vitronectin, fibronectin, and laminin. These studies indicated that cellular migration, axon growth and guidance, and neuronal differentiation can be enhanced through the incorporation of proteins and peptides that mimic the ECM. The present study has improved upon previous peptide work by integrating multiple ECM components to enhance the neuronal phenotype of the pluripotent cell type. As described herein the flexibility of the method has been demonstrated by characterizing films produced from four different peptides as well as an ability to combine multiple peptides in one material. In addition, the sol-gel method has many commercial advantages and this new "one pot" method using peptide silanes will enable a simple way to create a wide range of biologically active films.

The invention claimed is:

1. A method for preparing a peptide presenting sol-gel, said method comprising providing a peptide-silane composition; combining the peptide-silane composition with a second composition comprising silicates to form a mixture; coating the mixture onto a surface of a support; gelling the mixture to form a porous silica network presenting covalently bound peptides.

2. The method of claim 1 wherein said peptide-silane composition comprises a plurality of peptide-silane compounds that differ from one another by the sequence of the peptide moiety.

3. The method of claim 1 wherein the second composition comprises a silicate selected from the group consisting of tetraethylorthosilicate, tetramethylorthosilicate and tetrapropylorthosilicate.

4. The method of claim 3 where the peptide moiety of said peptide-silane comprises an amino acid sequence selected from the group consisting of RGD (SEQ ID NO:1), KDI (SEQ ID NO:2), YIG (SEQ ID NO:3), NID (SEQ ID NO:4), SLVRNRR (SEQ ID NO: 23) and CYFQRYLI (SEQ ID NO:6).

5. The method of claim 4 wherein the peptide moiety of said peptide-silane comprises an amino acid sequence selected from the group consisting of YIGSR (SEQ ID NO:7), GRGDNP (SEQ ID NO:8), RDIAEIIKDI (SEQ ID NO:9), RNNR (SEQ ID NO:5), CYFQRYLI (SEQ ID NO:6), NDNIDPNAVA (SEQ ID NO:10), YAVTGRGDSPAS (SEQ ID NO:11), RDIAEIIKDIG (SEQ ID NO:12), DPGYIG-SRGA (SEQ ID NO:13), ANDNIDPNAVAA (SEQ ID NO:14), AYAVTGRGDSPASA (SEQ ID NO:15), ARDIAEI-IKDIGA (SEQ ID NO:16) ADPGYIGSRGAA (SEQ ID NO:17), SIDRVEPYSSTAQG (SEQ ID NO: 18), CSVTCGG (SEQ ID NO: 19), VSWFSRHRYSPFAVS (SEQ ID NO: 20), AASIKVAVSADRG (SEQ ID NO: 21) and SLVRNRRVI-TIQG (SEQ ID NO: 22).

6. The method of claim 1 wherein the mixture is coated onto the surface of said support by dipping the support into said mixture and removing it.

7. The method of claim 6 further comprising the step of dipping the coated support into a second mixture wherein said second mixture has a different peptide-silane composition than mixture the support was dipped into first.

8. The method of claim 6 wherein the support is dipped into and removed from said mixture at a rate no faster than 35 mm/second.

9. A method for preparing a peptide presenting sol-gel having a predetermined concentration of a peptide covalently linked to the sol-gel, said method comprising providing a peptide-silane composition said peptide-silane is present at said predetermined concentration; combining the peptide-silane composition with a second composition comprising silicates to form a mixture; coating the mixture onto a surface of a support; gelling the mixture to form a porous sol-gel comprising covalently bound peptides at said predetermined concentration.

10. The method of claim 9 wherein said peptide-silane composition comprises a plurality of peptide-silane compounds that differ from one another by the sequence of the peptide moiety, wherein each of said plurality of peptide-silane compounds are covalently bound to the sol-gel at each predetermined concentration.

11. The method of claim 10 wherein said peptide-silane composition comprises 2 to 5 different peptide-silane compounds and said sol-gel comprises said 2 to 5 peptide-silane compounds covalently bound to the sol-gel at each of their predetermined concentrations.

12. The method of claim 10 wherein said peptide-silane composition comprises 3 to 4 different peptide-silane compounds and said sol-gel comprises said 3 to 4 peptide-silane compounds covalently bound to the sol-gel at each of their predetermined concentrations.

13. A kit for preparing a sol-gel having a defined concentration of peptides covalently bound to a sol-gel, said kit comprising a plurality of first containers, said first containers each comprising a unique peptide-silane compound; and a second container comprising silicates.

14. The kit of claim 13 wherein the second container comprises a silicate selected from the group consisting of tetraethylorthosilicate, tetramethylorthosilicate and tetrapropylorthosilicate.

15. The kit of claim 13 wherein the peptide-silane of each container comprises an amino acid sequence selected from the group consisting of RGD (SEQ ID NO:1), KDI (SEQ ID NO:2), YIG (SEQ ID NO:3), NID (SEQ ID NO:4), RNNR (SEQ ID NO:5), CYFQRYLI (SEQ ID NO:6), YIGSR (SEQ ID NO:7), GRGDNP (SEQ ID NO:8), RDIAEIIKDI (SEQ ID NO:9), NDNIDPNAVA (SEQ ID NO:10), YAVTGRGD-SPAS (SEQ ID NO:11), RDIAEIIKDIG (SEQ ID NO:12), DPGYIGSRGA (SEQ ID NO:13), ANDNIDPNAVAA (SEQ ID NO:14), AYAVTGRGDSPASA (SEQ ID NO:15), ARDI-AEIIKDIGA (SEQ ID NO:16) ADPGYIGSRGAA (SEQ ID NO:17), SIDRVEPYSSTAQG (SEQ ID NO: 18), CSVTCGG (SEQ ID NO: 19), VSWFSRHRYSPFAVS (SEQ ID NO: 20), AASIKVAVSADRG (SEQ ID NO: 21) and SLVRNRRVI-TIQG (SEQ ID NO: 22).

16. A nano-textured sol-gel material for cellular modulation formed from the process of claim 1, said sol-gel comprising: a peptide-silane complex covalently bound to said sol-gel.

17. The sol-gel hybrid material of claim 16, wherein the said peptide-silane comprises an amino acid sequence selected from the group consisting of RGD (SEQ ID NO:1), KDI (SEQ ID NO:2), YIG (SEQ ID NO:3), NID (SEQ ID NO:4), SLVNRR (SEQ ID NO: 23) and CYFQRYLI (SEQ ID NO:6).

18. The sol-gel hybrid material of claim 16 wherein the peptide moiety of said peptide-silane comprises an amino acid sequence selected from the group consisting of YIGSR (SEQ ID NO:7), GRGDNP (SEQ ID NO:8), RDIAEIIKDI (SEQ ID NO:9), NDNIDPNAVA (SEQ ID NO:10), YAVT-GRGDSPAS (SEQ ID NO:11), RDIAEIIKDIG (SEQ ID NO:12), DPGYIGSRGA (SEQ ID NO:13), ANDNIDP-NAVAA (SEQ ID NO:14), AYAVTGRGDSPASA (SEQ ID NO:15), ARDIAEIIKDIGA (SEQ ID NO:16) ADPGYIGSR-GAA (SEQ ID NO:17), SIDRVEPYSSTAQG (SEQ ID NO: 18), CSVTCGG (SEQ ID NO: 19), VSWFSRHRYSPFAVS (SEQ ID NO: 20), AASIKVAVSADRG (SEQ ID NO: 21) and SLVRNRRVITIQG (SEQ ID NO: 22).

19. The sol-gel hybrid material of claim 16 wherein the sol-gel comprises two or more different peptide-silanes covalently bound to the sol-gel.

20. The sol-gel hybrid material of claim 16 wherein the sol-gel comprises three different peptides covalently bound to the sol-gel, wherein said different peptides independently comprise an amino acid sequence selected from the group consisting of RNNR (SEQ ID NO:5), CYFQRYLI (SEQ ID NO:6), YIGSR (SEQ ID NO:7), GRGDNP (SEQ ID NO:8), RDIAEIIKDI (SEQ ID NO:9), NDNIDPNAVA (SEQ ID NO:10), YAVTGRGDSPAS (SEQ ID NO:11), RDIAEIIK-DIG (SEQ ID NO:12), DPGYIGSRGA (SEQ ID NO:13), ANDNIDPNAVAA (SEQ ID NO:14), AYAVTGRGDSPASA (SEQ ID NO:15), ARDIAEIIKDIGA (SEQ ID NO:16) ADPGYIGSRGAA (SEQ ID NO:17), SIDRVEPYSSTAQG (SEQ ID NO: 18), CSVTCGG (SEQ ID NO: 19), VSWFS-RHRYSPFAVS (SEQ ID NO: 20), AASIKVAVSADRG (SEQ ID NO: 21) and SLVRNRRVITIQG (SEQ ID NO: 22).

21. A sol-gel hybrid material produced by the method of claim 7.

22. The method of claim 1 wherein the peptide moiety of said peptide-silane is 6-30 amino acids in length.

23. The method of claim 1 wherein the peptide moiety of said peptide-silane is 6-14 amino acids in length.

* * * * *

SEQUENCE LISTING

```
<160> NUMBER OF SEQ ID NOS: 25

<210> SEQ ID NO 1
<211> LENGTH: 3
<212> TYPE: PRT
<213> ORGANISM: Artificial Sequence
<220> FEATURE:
<223> OTHER INFORMATION: Recognition sequence for fibronectin - various
      mammalian species

<400> SEQUENCE: 1

Arg Gly Asp
1

<210> SEQ ID NO 2
<211> LENGTH: 3
<212> TYPE: PRT
<213> ORGANISM: Artificial Sequence
<220> FEATURE:
<223> OTHER INFORMATION: Laminin recognition site - various mammalian
      species

<400> SEQUENCE: 2

Lys Asp Ile
1

<210> SEQ ID NO 3
<211> LENGTH: 3
<212> TYPE: PRT
<213> ORGANISM: Artificial Sequence
<220> FEATURE:
<223> OTHER INFORMATION: Laminin recognition site - various mammalian
      species

<400> SEQUENCE: 3

Tyr Ile Gly
1

<210> SEQ ID NO 4
<211> LENGTH: 3
<212> TYPE: PRT
<213> ORGANISM: Artificial Sequence
<220> FEATURE:
<223> OTHER INFORMATION: From extracellular matrix proteins, laminin and
      tenascin - various mammalian species
```

-continued

```
<400> SEQUENCE: 4

Asn Ile Asp
1

<210> SEQ ID NO 5
<211> LENGTH: 4
<212> TYPE: PRT
<213> ORGANISM: Artificial Sequence
<220> FEATURE:
<223> OTHER INFORMATION: Laminin recognition sequence - various
      mammalian species

<400> SEQUENCE: 5

Arg Asn Asn Arg
1

<210> SEQ ID NO 6
<211> LENGTH: 8
<212> TYPE: PRT
<213> ORGANISM: Artificial Sequence
<220> FEATURE:
<223> OTHER INFORMATION: Laminin recognition sequence - various
      mammalian species

<400> SEQUENCE: 6

Cys Tyr Phe Gln Arg Tyr Leu Ile
1               5

<210> SEQ ID NO 7
<211> LENGTH: 5
<212> TYPE: PRT
<213> ORGANISM: Artificial Sequence
<220> FEATURE:
<223> OTHER INFORMATION: Laminin recognition site - various mammalian
      species

<400> SEQUENCE: 7

Tyr Ile Gly Ser Arg
1               5

<210> SEQ ID NO 8
<211> LENGTH: 6
<212> TYPE: PRT
<213> ORGANISM: Artificial Sequence
<220> FEATURE:
<223> OTHER INFORMATION: Recognition sequence for fibronectin - various
      mammalian species

<400> SEQUENCE: 8

Gly Arg Gly Asp Asn Pro
1               5

<210> SEQ ID NO 9
<211> LENGTH: 10
<212> TYPE: PRT
<213> ORGANISM: Artificial Sequence
<220> FEATURE:
<223> OTHER INFORMATION: Laminin recognition site - various mammalian
      species

<400> SEQUENCE: 9

Arg Asp Ile Ala Glu Ile Ile Lys Asp Ile
1               5                   10

<210> SEQ ID NO 10
<211> LENGTH: 10
<212> TYPE: PRT
<213> ORGANISM: Artificial Sequence
```

-continued

```
<220> FEATURE:
<223> OTHER INFORMATION: From extracellular matrix proteins, laminin and
      tenascin - various mammalian species

<400> SEQUENCE: 10

Asn Asp Asn Ile Asp Pro Asn Ala Val Ala
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Recognition sequence for fibronectin - various
      mammalian species

<400> SEQUENCE: 11

Tyr Ala Val Thr Gly Arg Gly Asp Ser Pro Ala Ser
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Laminin recognition site - various mammalian
      species

<400> SEQUENCE: 12

Arg Asp Ile Ala Glu Ile Ile Lys Asp Ile Gly
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Laminin recognition site - various mammalian
      species

<400> SEQUENCE: 13

Asp Pro Gly Tyr Ile Gly Ser Arg Gly Ala
1               5                   10

<210> SEQ ID NO 14
<211> LENGTH: 12
<212> TYPE: PRT
<213> ORGANISM: Artificial Sequence
<220> FEATURE:
<223> OTHER INFORMATION: From extracellular matrix proteins, laminin and
      tenascin - various mammalian species

<400> SEQUENCE: 14

Ala Asn Asp Asn Ile Asp Pro Asn Ala Val Ala Ala
1               5                   10

<210> SEQ ID NO 15
<211> LENGTH: 14
<212> TYPE: PRT
<213> ORGANISM: Artificial Sequence
<220> FEATURE:
<223> OTHER INFORMATION: Recognition sequence for fibronectin - various
      mammalian species

<400> SEQUENCE: 15

Ala Tyr Ala Val Thr Gly Arg Gly Asp Ser Pro Ala Ser Ala
1               5                   10
```

```
<210> SEQ ID NO 16
<211> LENGTH: 13
<212> TYPE: PRT
<213> ORGANISM: Artificial Sequence
<220> FEATURE:
<223> OTHER INFORMATION: Laminin recognition site - various mammalian
      species

<400> SEQUENCE: 16

Ala Arg Asp Ile Ala Glu Ile Ile Lys Asp Ile Gly Ala
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Laminin recognition site - various mammalian
      species

<400> SEQUENCE: 17

Ala Asp Pro Gly Tyr Ile Gly Ser Arg Gly Ala Ala
1               5                   10

<210> SEQ ID NO 18
<211> LENGTH: 14
<212> TYPE: PRT
<213> ORGANISM: Artificial Sequence
<220> FEATURE:
<223> OTHER INFORMATION: NCAM recognition sequence - various mammalian
      species

<400> SEQUENCE: 18

Ser Ile Asp Arg Val Glu Pro Tyr Ser Ser Thr Ala Gln Gly
1               5                   10

<210> SEQ ID NO 19
<211> LENGTH: 7
<212> TYPE: PRT
<213> ORGANISM: Artificial Sequence
<220> FEATURE:
<223> OTHER INFORMATION: Thrombospondin recognition sequence

<400> SEQUENCE: 19

Cys Ser Val Thr Cys Gly Gly
1               5

<210> SEQ ID NO 20
<211> LENGTH: 17
<212> TYPE: PRT
<213> ORGANISM: Artificial Sequence
<220> FEATURE:
<223> OTHER INFORMATION: Laminin recognition sequence - various
      mammalian species

<400> SEQUENCE: 20

Val Ser Trp Phe Ser Arg His Ile Ser Arg Tyr Ser Pro Phe Ala Val
1               5                   10                  15

Ser

<210> SEQ ID NO 21
<211> LENGTH: 13
<212> TYPE: PRT
<213> ORGANISM: Artificial Sequence
<220> FEATURE:
<223> OTHER INFORMATION: Laminin recognition sequence - various
      mammalian species
```

```
<400> SEQUENCE: 21

Ala Ala Ser Ile Lys Val Ala Val Ser Ala Asp Arg Gly
1               5                   10

<210> SEQ ID NO 22
<211> LENGTH: 13
<212> TYPE: PRT
<213> ORGANISM: Artificial Sequence
<220> FEATURE:
<223> OTHER INFORMATION: Laminin recognition sequence - various
      mammalian species

<400> SEQUENCE: 22

Ser Leu Val Arg Asn Arg Arg Val Ile Thr Ile Gln Gly
1               5                   10

<210> SEQ ID NO 23
<211> LENGTH: 7
<212> TYPE: PRT
<213> ORGANISM: Artificial Sequence
<220> FEATURE:
<223> OTHER INFORMATION: Laminin recognition sequence - various
      mammalian species

<400> SEQUENCE: 23

Ser Leu Val Arg Asn Arg Arg
1               5

<210> SEQ ID NO 24
<211> LENGTH: 4
<212> TYPE: PRT
<213> ORGANISM: Artificial Sequence
<220> FEATURE:
<223> OTHER INFORMATION: Laminin recognition sequence - various
      mammalian species

<400> SEQUENCE: 24

Ser Asn Asn Arg
1

<210> SEQ ID NO 25
<211> LENGTH: 17
<212> TYPE: PRT
<213> ORGANISM: Artificial Sequence
<220> FEATURE:
<223> OTHER INFORMATION: Laminin recognition sequence - various
      mammalian species

<400> SEQUENCE: 25

Arg Asp Ile Ala Glu Ile Ile Lys Asp Ile Ser Leu Val Arg Asn Arg
1               5                   10                  15

Arg
```